United States Patent
Munne et al.

(10) Patent No.: US 10,918,327 B2
(45) Date of Patent: Feb. 16, 2021

(54) COMPOSITIONS AND METHODS FOR DETERMINING RECEPTIVITY OF AN ENDOMETRIUM FOR EMBRYONIC IMPLANTATION

(71) Applicant: CooperSurgical, Inc., Trumbull, CT (US)

(72) Inventors: Santiago Munne, Short Hills, NJ (US); Joson A. Horcajadas, Seville (ES); Jon Aizpurua, Alicante (ES)

(73) Assignee: CooperSurgical, Inc., Trumbull, CT (US)

( * ) Notice: Subject to any disclaimer, the term of this patent is extended or adjusted under 35 U.S.C. 154(b) by 161 days.

(21) Appl. No.: 15/887,087

(22) Filed: Feb. 2, 2018

(65) Prior Publication Data

US 2018/0214068 A1   Aug. 2, 2018

Related U.S. Application Data

(60) Provisional application No. 62/453,631, filed on Feb. 2, 2017.

(51) Int. Cl.
| | |
|---|---|
| *A61B 5/00* | (2006.01) |
| *G16H 10/40* | (2018.01) |
| *C12Q 1/6806* | (2018.01) |
| *B01L 3/00* | (2006.01) |
| *G01N 33/50* | (2006.01) |
| *C12Q 1/6883* | (2018.01) |
| *G01N 33/68* | (2006.01) |
| *G16H 50/30* | (2018.01) |
| *G16H 50/70* | (2018.01) |
| *C07K 14/59* | (2006.01) |
| *G16H 20/10* | (2018.01) |

(52) U.S. Cl.
CPC ...... *A61B 5/4325* (2013.01); *B01L 3/502753* (2013.01); *C12Q 1/6806* (2013.01); *C12Q 1/6883* (2013.01); *G01N 33/5023* (2013.01); *G01N 33/689* (2013.01); *G16H 10/40* (2018.01); *G16H 50/30* (2018.01); *G16H 50/70* (2018.01); *A61B 5/4343* (2013.01); *A61B 5/7275* (2013.01); *B01L 2300/0819* (2013.01); *C07K 14/59* (2013.01); *C12Q 2600/112* (2013.01); *C12Q 2600/158* (2013.01); *G16H 20/10* (2018.01)

(58) Field of Classification Search
None
See application file for complete search history.

(56) References Cited

U.S. PATENT DOCUMENTS

| | | | |
|---|---|---|---|
| 2012/0040849 A1 | 2/2012 | Simon Valles et al. | |
| 2016/0097102 A1* | 4/2016 | Suh | C12Q 1/6886 424/133.1 |

OTHER PUBLICATIONS

Horcajadas et al., "Global gene expression profiling of human endometrial receptivity" 63 Journal of Reproductive Immunology 41-49 (2004).*

Enciso et al., "Development of a new comprehensive and reliable endometrial receptivity map (ER Map/ER Grade) based on RT-qPCR gene expression analysis," *Human Reproduction*, Feb. 1, 2018, 33(2): 220-228.

* cited by examiner

*Primary Examiner* — Nancy J Leith
(74) *Attorney, Agent, or Firm* — Fish & Richardson P.C.

(57) ABSTRACT

Provided herein are methods and kits for determining receptivity status of an endometrium for embryonic implantation.

23 Claims, 3 Drawing Sheets
(3 of 3 Drawing Sheet(s) Filed in Color)

COMPOSITIONS AND METHODS FOR DETERMINING RECEPTIVITY OF AN ENDOMETRIUM FOR EMBRYONIC IMPLANTATION

CLAIM OF PRIORITY

This application claims the benefit of U.S. Provisional Patent Application Ser. No. 62/453,631, filed on Feb. 2, 2017. The entire contents of the foregoing are hereby incorporated by reference.

TECHNICAL FIELD

The present disclosure relates generally to the fields of reproductive medicine. More specifically, this disclosure relates to in vitro methods and kits for determining the receptivity status of an endometrium for embryonic implantation.

BACKGROUND

The endometrium reaches a receptive status for embryonic implantation around day 19-21 of the menstrual cycle. The number of molecular diagnostic tools available to characterize the receptive status for embryonic implantation is very limited and lack key elements for the accurate determination of the window of implantation (WOI), such as immune response genes, crucial for embryo implantation.

SUMMARY

In one aspect, the disclosure provides methods of predicting endometrial receptivity for transplantation of a pre-implantation embryo.

Provided herein are methods of predicting endometrial receptivity status for embryonic implantation in a human subject that include: (a) providing a first biological sample obtained from a human subject at a first time point within a menstrual cycle; (b) determining the gene expression profile of a panel of genes in the first biological sample, wherein the panel of genes consists of: Annexin A4 (ANXA4), Cation channel sperm auxiliary subunit beta (CATSPERB), Prostaglandin F receptor (PTGFR), Prostaglandin-endoperoxide synthase 1 (prostaglandin G/H synthase and cyclooxygenase) (PTGS1), Interleukin-8 (IL8), Secretoglobin, family 2A, member 2 (SCGB2A2), Angiopoietin-like 1 (ANGPTL1), Hypoxanthine phosphoribosyltransferase 1 (HPRT1), Matrix metallopeptidase 10 (MMP10), Progesterone Receptor (PGR), Integrin alpha 8 (ITGA8), Interferon gamma (IFNG), Prokineticin-1 (PROK1), Forkhead box protein O1 (FOXO1), C-X-C motif chemokine ligand 1 (CXCL1), Stanniocalcin-1 (STC1), Matrix Metallopeptidase 9 (MMP9), Mucin 1 (MUC1), Ribosomal protein L13a (RPL13A), Calcitonin-related polypeptide alpha (CALCA), Integrin subunit alpha-9 (ITGA9), Rac GTPase-activating protein 1 (RACGAP1), Glutathione peroxidase 3 (GPX3), Protein phosphatase 2, regulatory subunit B, gamma (PPP2R2C), Arginase 2 (ARG2), Secretoglobin, family 3A, member 1 (SCGB3A1), Aldehyde dehydrogenase family 1 member A3 (ALDH1A3), Apolipoprotein D (APOD), C2 calcium-dependent domain-containing protein 4B (C2CD4B), Trefoil factor 3 (TFF3), Aquaporin-3 (AQP3), Gap junction protein, alpha 4 (GJA4), Rho GDP-dissociation inhibitor alpha (ARHGDIA), Selectin L (SELL), Apolipoprotein L, 2 (APOL2), Metallothionein-1H (MT1H), Metallothionein-1X (MT1X), Metallothionein-1L (MT1L), Monoamine oxidase AA (MAOA) and Metallothionein-1F (MT1F) using reverse transcription polymerase chain reaction (RT-qPCR) analysis; and (c) identifying the human subject as having: (i) a receptive endometrial status, wherein the determined gene expression profile corresponds to a gene expression profile of the panel of genes of a receptive endometrial receptivity reference group, (ii) a non-receptive endometrial status, wherein the determined gene expression profile corresponds to a gene expression profile of the panel of genes of a non-receptive endometrial receptivity reference group, (iii) a pre-receptive endometrial status, wherein the determined gene expression profile corresponds to a gene expression profile of the panel of genes of a pre-receptive endometrial receptivity reference group, or (iv) a post-receptive endometrial status, wherein the determined gene expression profile corresponds to a gene expression profile of the panel of genes of a post-receptive endometrial receptivity reference group.

In some embodiments, the first biological sample is an endometrial biopsy obtained from the uterine fundus.

In some embodiments, the human subject has undergone assisted reproductive treatment, and the first time point is seven days after a luteinizing hormone surge.

In some embodiments, the human subject has undergone assisted reproductive treatment, and the first time point is seven days after administration of human chorionic gonadotropin (hCG).

In some embodiments, the human subject has undergone hormone replacement therapy cycles, and the first time point is five days after progesterone impregnation.

In some embodiments of any of the methods described herein, the method further includes after identifying the human subject as having a receptive endometrial status, (d) transferring a pre-implantation embryo into the identified human subject.

In some embodiments of any of the methods described herein, the method further includes after identifying the human subject as having a non-receptive endometrial status, a pre-receptive endometrial status, or a post-receptive endometrial status, (d) obtaining a second biological sample from the human subject at a second time point and repeating steps (b) and (c) on the second biological sample.

In some embodiments of any of the methods described herein, the method further includes after identifying the human subject has having a receptive endometrial status, (e) transferring a pre-implantation embryo into the identified human subject.

In some embodiments, the second biological sample is an endometrial biopsy obtained from the uterine fundus.

In some embodiments, the subject is identified as having a post-receptive endometrial status, and the second biological sample is obtained in another menstrual cycle one or two days before the first biological sample was taken in the previous menstrual cycle.

In some embodiments, the subject is identified as having a pre-receptive endometrial status, and the second biological sample is obtained in another menstrual cycle one or two days after the first biological sample was taken in the previous menstrual cycle.

In some embodiments wherein the subject is identified as having a non-receptive endometrial status, the method further includes instructing a healthcare professional to select a treatment plan for the identified subject.

In some embodiments wherein the subject is identified as having a non-receptive endometrial status, the method further includes selecting a treatment plan for the identified subject. In some embodiments, the treatment plan includes a hormone replacement therapy cycle.

In some embodiments, the subject has a history of miscarriages or stillbirths, and/or a history of fertility issues.

In some embodiments, the subject has had one or more cycles of in vitro fertilization (IVF).

In some embodiments, the subject has previously not had IVF.

In some embodiments, the determining step occurs on a chip, an array, a multi-well plate, or a tube (e.g., a microcentrifuge tube). In some embodiments, the determining step of each gene within the panel of genes is performed in a reaction volume of 0.005 µL to 100 µL. In some embodiments, the determining step of each gene within the panel of genes is performed in a reaction volume of 0.005 µL to 50 µL.

In some embodiments, the determining step is performed using a computer-assisted algorithm. In some embodiments, the determining step is performed using principal component analysis and/or discriminant functional analysis.

In some embodiments of any of the methods described herein, the method further includes modifying the subject's clinical record to identify the subject as having or not having a receptive endometrial status, as having or not having a post-receptive endometrial status, as having or not having a pre-receptive endometrial status, or as having or not having a non-receptive endometrial status. The clinical record may be stored in any suitable data storage medium (e.g., a computer readable medium).

Also provided herein are kits that include reagents suitable for determining an endometrial gene expression profile of a panel of genes, wherein the panel of genes consists of: ANXA4, CATSPERB, PTGFR, PTGS1, IL8, SCGB2A2, ANGPTL1, HPRT1, MMP10, PGR, ITGA8, IFNG, PROK1, FOXO1, CXCL1, STC1, MMP9, MUC1, RPL13A, CALCA, ITGA9, RACGAP1, GPX3, PPP2R2C, ARG2, SCGB3A1, ALDH1A3, APOD, C2CD4B, TFF3, AQP3, GJA4, ARHGDIA, SELL, APOL2, MT1H, MT1X, MT1L, MAOA and MT1F in a biological sample obtained from a subject.

In some embodiments of any of the kits described herein, the kit further includes reagents suitable for determining an endometrial gene expression profile of the panel of genes for a set of reference groups, wherein the set of reference groups includes a receptive endometrial reference group, a non-receptive endometrial reference group, a pre-receptive endometrial reference group and a post-receptive endometrial reference group. In some embodiments, the biological sample is an endometrial biopsy obtained from the uterine fundus.

In some embodiments, the reagents are suitable for reverse transcription polymerase chain reaction.

In some embodiments of any of the kits described herein, the kit can further include a chip, an array, a multi-well plate or a tube (e.g., a microcentrifuge tube).

In some embodiments of any of the kits described herein, the kit can further include instructions for use of the kit according to any of the methods described herein.

Also provided in aspects of the invention are panels of genes useful for predicting endometrial receptivity for embryonic implantation in a human subject. By "a panel of genes" it is meant a collection, or combination, of two or more genes, e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, or forty genes, whose gene expression profile in a biological sample (e.g., an endometrial tissue biopsy sample) is associated with endometrial receptivity. The panel of genes (e.g., panel A) described herein may be used to provide a prediction of endometrial receptivity of a human subject, to monitor a subject with fertility issues (e.g., recurrent miscarriages, recurrent failed cycles of in vitro fertilization (IVF)), to monitor a subject undergoing IVF, to provide a prognosis to a human subject having a receptive endometrial status, to provide a prognosis to a human subject having a non-receptive endometrial status, to provide a prognosis to a human subject having a pre-receptive endometrial status, to provide a prognosis to a human subject having a post-receptive endometrial status.

In some embodiments, the methods include instructing a healthcare professional (e.g., a physician, physician assistant, nurse practitioner, nurse and case manager) to select a treatment plan for a subject. For example, the methods may further include selecting a treatment plan for a subject, which includes selectively administering a hormone replacement therapy (e.g., progesterone and estrogen), and/or performing a fertility evaluation, which includes, for example, performing a procedure selected from the group consisting of: an ultrasound, a hysterosalpingogram, a hysteroscopy and a hormone blood test. The treatment plan can include prescribing to the subject therapeutic lifestyle changes to improve fertility (e.g., dietary changes, weight loss or weight gain).

As used herein, the term "biological sample" refers to a sample obtained or derived from a subject. By way of example, the sample may be selected from the group consisting of body fluids (e.g., blood, whole blood, plasma, serum, mucus secretions, urine, or saliva) and tissue (e.g., an endometrial tissue biopsy sample). In some embodiments, the sample is, or includes a blood sample. The preferred biological source is an endometrial tissue biopsy sample.

The term "subject" as used herein refers to a mammal. A subject therefore refers to, for example, dogs, cats, horses, cows, pigs, guinea pigs, humans and the like. When the subject is a human, the subject may be referred to herein as a patient. The human subject can be genetically female (having XX sex chromosomes, or XXY sex chromosomes), premenopausal, and/or of advanced maternal age (e.g., over 35 years of age). For example, the human subject can have a history of miscarriages or stillbirths, a history of fertility issues/complications (e.g., pelvic inflammatory disease, endometriosis, polycystic ovarian syndrome, hormonal imbalances, premature ovarian aging/failure, antiphospholipid syndrome), and/or has previously had assisted reproductive treatments and/or hormone replacement therapies. In some examples, the human subject has had one or more cycles of IVF. In other examples, the subject has not had IVF.

As used herein, "obtain" or "obtaining" can be any means whereby one comes into possession of the sample by "direct" or "indirect" means. Directly obtaining a sample means performing a process (e.g., performing a physical method such as extraction) to obtain the sample. Indirectly obtaining a sample refers to receiving the sample from another party or source (e.g., a third party laboratory that directly acquired the sample). Directly obtaining a sample includes performing a process that includes a physical change in a physical substance, e.g., a starting material, such as a tissue biopsy, (e.g., endometrial biopsy that was previously isolated from a patient). Thus, obtain is used to mean collection and/or removal of the sample from the subject.

As used herein the term "reference group" refers to a group of endometrial tissue biopsy samples that are obtained from a group of individuals for which the endometrial status is known. A "receptive endometrial reference group" means that the gene expression profile of the selected genes (e.g., panel A) is for a group of individuals with a receptive endometrial status. A "non-receptive endometrial reference group" means that the gene expression profile of the selected genes (e.g., panel A) is for a group of individuals with non-receptive endometrial status. A "pre-receptive endometrial reference group" means that the gene expression profile of the selected genes (e.g., panel A) is for a group of individuals with pre-receptive endometrial status. A "post-receptive endometrial reference group" means that the gene expression profile of the selected genes (e.g., panel A) is for a group of individuals with a post-receptive endometrial status.

As used herein, the phrase "receptive endometrial status" means that the window of implantation matches the day on which the biopsy was taken, and that the subject's uterus is receptive for embryonic implantation. For example, a receptive endometrial status is defined as an endometrial status that is observed 7 days after the luteinizing hormone (LH) surge in a natural menstrual cycle of 28 days.

The phrase "pre-receptive endometrial status" means that the window of implantation has not yet been reached on the day on which the biopsy was taken, and that the subject's uterus is not receptive for embryonic implantation. A pre-receptive endometrial status is defined as an endometrial status that is observed in the days prior to the window of implantation during the secretory phase of a menstrual cycle.

The phrase "post-receptive endometrial status" means that the window of implantation has already passed on the day on which the biopsy was taken, and that the subject's uterus is not receptive for embryonic implantation. A post-receptive endometrial status is defined as an endometrial status that is observed in the days following the window of implantation during the secretory phase of a menstrual cycle.

The phrase "non-receptive endometrial status" means that the day on which the biopsy was taken was during the proliferative phase of a menstrual cycle, and that the subject's uterus is not receptive for embryonic implantation.

A "luteinizing hormone (LH) surge" can be determined using various methods known in the art, including by urine and/or blood testing, in order to detect the expression and/or presence of LH in a sample, and/or to quantify the amount of LH present in a sample. Expression and/or presence of LH can be detected using known assays that include antibodies targeting LH. Kits for determining a LH surge are commercially available and known to those in the art.

The phrase "the endometrial gene expression profile corresponds to an endometrial gene expression profile of the panel of genes of a reference group" means that the endometrial gene expression profile of a sample is predicted based on computer-assisted algorithms (e.g., principle component analysis, or any other classification algorithms known in the art) to fall within the classification of the endometrial gene expression profile of a reference group (e.g., a receptive endometrial reference group, a non-receptive endometrial reference group, a pre-receptive endometrial reference group, a post-receptive endometrial reference group).

As used herein, the phrase "assisted reproductive treatment (ART)" refers to a plurality of treatments that may facilitate fertility treatment. Non-limiting examples of ART include in vitro fertilization (IVF), gamete intrafallopian transfer (GIFT), zygote intrafallopian transfer (ZIFT), surrogacy, pre-implantation genetic testing, in vitro oocyte maturation, and hormone replacement therapy (HRT) cycles (e.g., exogenous administration of progesterone and estrogen).

As used herein the term "subfertile" refers to a subject who has difficulty getting pregnant or carrying a pregnancy to full-term. For example, a subject may be subfertile because of endometriosis, ovulatory disorders, tubal disease, peritoneal adhesion, and/or uterine abnormalities. For example, a subject may be subfertile if the subject is of advanced age (i.e. over 35 years of age).

As used herein the term "pre-implantation embryo" refers to an embryo that was fertilized in vitro. In some embodiments, a pre-implantation embryo is a blastocyst (i.e. an embryo of 5-7 days post fertilization). In some embodiments, the pre-implantation embryo was genetically profiled by pre-implantation genetic screening and/or diagnosis prior to transfer to the uterus of a subject identified as having a receptive endometrial status.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
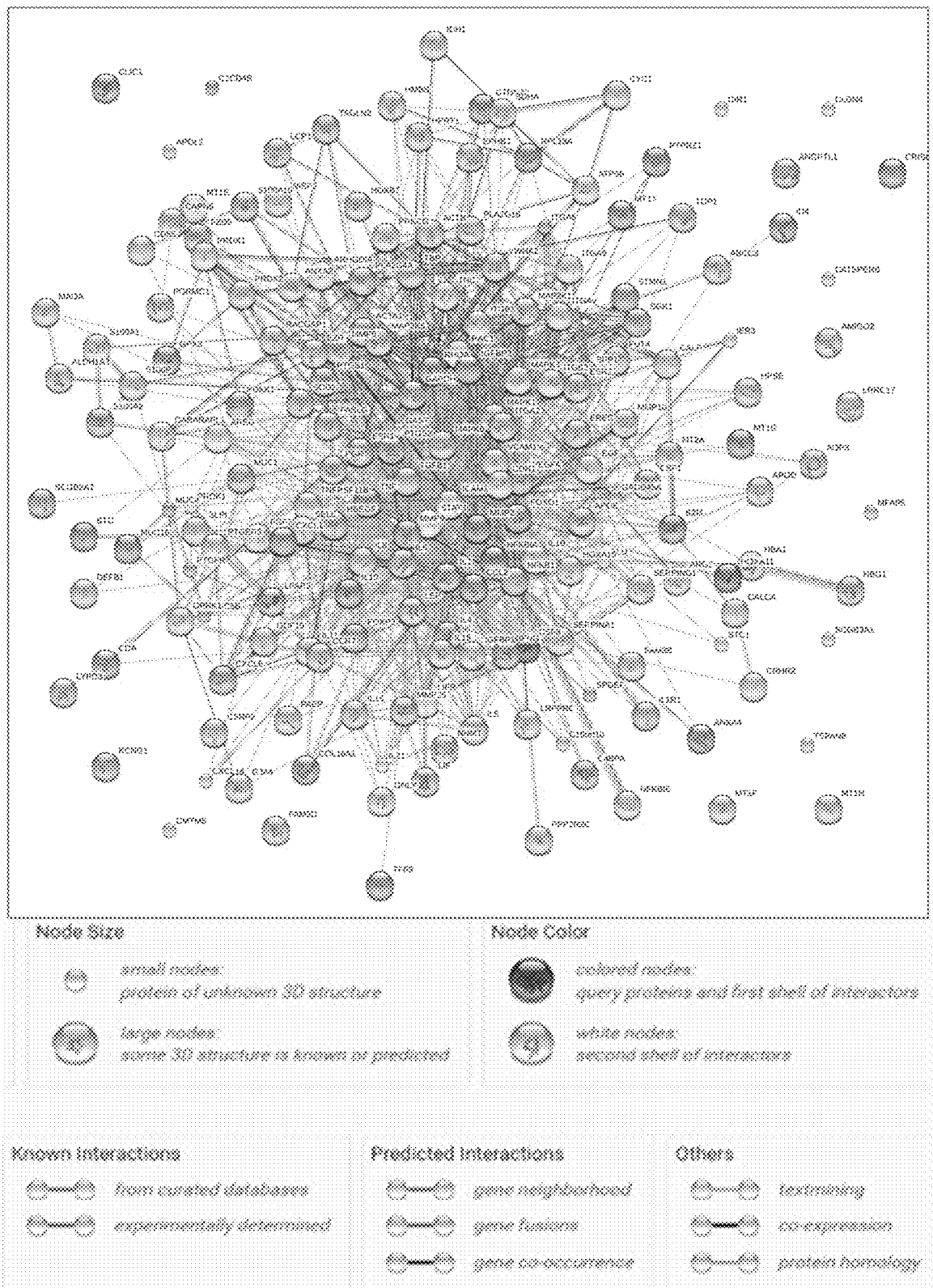
FIG. 1 is a representative STRING database generated protein interaction network of the proteins codified by the 184 WO1 selected genes.

The present disclosure is based, in part, on the unexpected discovery that it is possible to determine the receptivity status of an endometrium for embryonic implantation by combined qRT-PCR expression analysis of genes involved in endometrial proliferation and immune response.

One of the key processes for the establishment of a successful pregnancy is embryonic implantation into the endometrium. Implantation is a complex process that involves an intricate dialogue between the embryo and the endometrial cells (Singh et al., *J Endocrinol* 2011; 210:5-14). This interaction is required for the apposition, adhesion and invasion of the blastocyst (Giudice and Irwin, *Semin Reprod Endocrinol* 1999; 17:13-21).

The human endometrium is a highly dynamic structure, which undergoes periodical changes during menstrual cycle in order to reach a receptive status adequate for embryonic implantation. This period of receptivity is known as the window of implantation (WOI) and occurs between Day 19 and Day 21 of the menstrual cycle (Navot et al., *Fertil Steril* 1991; 55:114-118; Harper, *Baillieres Clin Obstet Gynaecol* 1992; 6:351-371; Giudice, *Hum Reprod* 1999; 14 Suppl 2:3-16). In any other phase of the menstrual cycle, the endometrium is reluctant to pregnancy (Garrido-Gómez et al., *Fertil Steril* 2013; 99:1078-1085). Successful implantation requires therefore a viable embryo and synchrony between it and the receptive endometrium (Teh et al., *J Assist Reprod Genet* 2016; 33:1419-1430). The correct identification and prediction of the period of uterine receptivity is essential to maximize the effectiveness of assisted reproduction treatments (ART).

The study of endometrial receptivity is not new as histological analysis has been traditionally used for endometrial dating (Noyes et al., *Fertil Steril* 1950; 1:3-25); however, the accuracy of this method to predict endometrial receptivity has been shown to be limited (Coutifaris et al., *Fertil Steril* 2004; 82:1264-1272; Murray et al., *Fertil Steril* 2004; 81:1333-1343). Some alternative methods to evaluate endometrial receptivity have been developed in the last decade, these methods include: biochemical markers such as molecules involved in calcium sensing and signal transduction (Zhang et al., *Reprod Biol Endocrinol* 2012; 10:106), soluble ligands (Thouas et al., *Endocr Rev* 2015; 36:92-130), hormone receptors (Aghajanova et al., *Fertil Steril* 2009; 91:2602-2610), cytokines (Jones et al., *J Clin Endocrinol Metab* 2004; 89:6155-6167; Lédée-Bataille et al., *Fertil Steril* 2005; 83:598-605; Paiva et al., *Hum Reprod* 2011; 26:1153-1162), microRNAs (Sha et al., *Fertil Steril* 2011; 96; Kresowik et al., *Biol Reprod* 2014; 91:20-24) or HOX-class homeobox genes (Kwon and Taylor, *Ann N Y Acad Sci* 2004; 1034: p. 1-18; Xu et al., *Hum Reprod* 2014; 29:781-790).

Other studies, focused on the understanding of the molecular mechanisms underlying the histological changes observed in the endometrium during the menstrual cycle, have identified specific genes responsible for the alterations observed (Talbi et al., *Endocrinology* 2006; 147:1097-1121; Zhang et al., *Mol Reprod Dev* 2013; 80:8-21). Some other reports have addressed this molecular analysis from a wider perspective, performing a global screening of the transcriptome at different moments of the menstrual cycle (Carson, *Mol Hum Reprod* 2002; 8:871-879; Ponnampalam et al., *Mol Hum Reprod* 2004; 10:879-893; Mirkin et al., *Hum Reprod* 2005; 20:2104-2117; Talbi et al., *Endocrinology* 2006; 147: 1097-1121; Haouzi et al., *Hum Reprod* 2009; 24:198-205), under different infertility conditions (Koler et al., *Hum Reprod* 2009; 24:2541-2548; Altmäe et al., *Mol Hum Reprod* 2010; 16:178-187; Roy et al., *Hum Reprod* 2014; 29:2431-2438; Tapia-Pizarro et al., *Reprod Biol Endocrinol* 2014; 12:92; Koot et al., *Sci Rep* 2016; 6:19411), pathologies (Kao et al., 2003; Sun et al., *Fertil Steril* 2014; 101; Garcia-Velasco et al., *Reprod Biomed Online* 2015; 31:647-654) or ovarian stimulation protocols (Mirkin et al., *J Clin Endocrinol Metab* 2004; 89:5742-5752; Horcajadas et al., *Mol Hum Reprod* 2005; 11:195-205; Liu et al., *Fertil Steril* 2008; 90:2152-2164; Haouzi et al., *Hum Reprod* 2009; 24:1436-1445). Valuable information about the process of endometrial proliferation can be extracted from these studies. However, even though the list of studies published in this topic is long, the number of molecular diagnostic tools to identify the moment of uterine receptivity is reduced (Lessey et al., *Fertil Steril* 1995; 63:535-542; Lessey et al., *Fertil Steril* 2000; 73:779-787; Dubowy et al., *Fertil Steril* 2003; 80:146-156; Diaz-Gimeno et al., *Fertil Steril* 2011; 95:50-60, 60-15). Some studies looking at the utility of single molecule markers for endometrial receptivity have concluded that a single molecule may not suffice to describe a complex phenomenon like receptivity (Brinsden et al., *Fertil Steril* 2009; 91:1445-1447) and, in this sense, transcriptomic profiles may be a more reliable tool.

Most global transcriptomic analyses of the endometrium have been performed using an unselected source of genes involved in many biological processes, but not specifically expressed in the endometrial tissue or related to the process of endometrial receptivity acquisition. The selection of genes, specifically described to be expressed in the endometrium during the WOI and involved in the process of embryonic implantation, was chosen as a better strategy to accurately define the transcriptomic signature of the receptive endometrium and also to develop a reliable diagnostic tool for endometrial receptivity. Processes such as endometrial proliferation and immune response have been described as essential for endometrial preparation and embryonic implantation, so a selection of genes involved in those processes could provide interesting biological and clinical information about the process of endometrial receptivity (Sign et al., 2011; and Haller-Kikkatalo et al., *Semin Reprod Med* 2014; 32: 376-384).

For global endometrial transcriptomic analyses, the preferred technique has been gene expression microarrays (Sherwin et al., *Reproduction* 2006; 132:1-10; Horcajadas et al., *Hum Reprod Updat* 2007; 13:77-86; Haouzi et al., *Reprod Biomed Online* 2012; 24:23-34).

RT-qPCR has been shown to have the widest dynamic range, the lowest quantification limits and the least biased results and hence it is considered the gold standard method for gene expression analysis. In this context, we believe the use of RT-qPCR may be a more robust and reliable technique for the analysis of the expression of genes relevant for the process of endometrial receptivity and, also, for the development of diagnostic tools based on the identification of specific signatures associated to different endometrial status.

Without wishing to be bound by theory, the present inventors defined a new system for human endometrial receptivity evaluation, based on the analysis of the expression of genes related to endometrial proliferation and the immunological response associated to embryonic implantation using a high throughput RT-qPCR platform. A comprehensive solution to analyze the endometrial transcriptomic signature at the WOI was explored. Validation was achieved on 306 endometrial samples including fertile women and patients undergoing fertility treatment between July 2014 and March 2016. Expression analyses of 184 genes involved in endometrial receptivity and immune response were performed. Samples were additionally tested with an independent endometrial receptivity test. Gene ontology analyses revealed that cellular proliferation, response to wounding, defence and immune response are the most over-represented biological terms in the group of genes selected. Significantly different gene expression levels (fold change) were found in 85 out of 184 selected genes when comparing LH+2 and LH+7 samples (Paired t-test, p<0.05). Principal component analysis (PCA) and discriminant functional analysis revealed that 40 of the differentially expressed genes allowed accurate classification of samples into 4 endometrial status: proliferative, pre-receptive, receptive and post-receptive in both groups, fertile women and infertile patients.

The identification of the optimal time for embryo transfer is essential to maximize the effectiveness of assisted reproductive technologies. For successful embryo implantation, a healthy embryo at blastocyst state and a functional endometrium ready to receive it, are required. There is growing evidence that shows the importance of embryonic-endometrial synchrony for the achievement of a successful pregnancy (Navot et al., *Fertil Steril* 1991; 55:114-118; Prapas et al., *Hum Reprod* 1998; 13:720-723; Wilcox et al., *N Engl J Med* 1999; 340:1796-1799; Shapiro et al., *Fertil Steril* 2008; 89:20-26; Shapiro et al., *Reprod Biomed Online* 2014; 29:286-290; *Reprod Biomed Online* 2016; 33:50-55; Franasiak et al., *Fertil Steril* 2013; 100:597; Healy et al., *Hum Reprod* 2017; 32:362-367). This concept, however, has yet to be taken into the IVF clinical practice. Much effort is put in the production and selection of the most competent embryo to be transferred (Chen et al., Fragouli and Wells, *Semin Reprod Med* 2012; 30:289-301; Cruz et al., *J Assist Reprod Genet* 2011; 28:569-573; and Forman et al., *Fertil Steril* 2013; 100:100-107), but little attention is paid to the other essential part of the pregnancy; no detailed analysis of the functionality of the endometrium or the period of uterine receptivity is routinely performed in IVF centers. The identification of the optimal time for embryo transfer is essential to maximize the effectiveness of ART.

The present disclosure relates to methods useful for the characterization of (e.g., clinical evaluation, diagnosis, classification, prediction, or profiling) of endometrial receptivity based on the gene expression profile of a panel of genes (e.g., panel A). The panel of genes described herein are particularly useful for characterizing (e.g., assessing or predicting) a subject for having a receptive status for embryonic implantation. Thus, in some aspects, the disclosure provides methods that include determining the gene expression profile of a selected panel of genes in a biological sample obtained from a subject, wherein a panel comprises a plurality of genes associated with endometrial receptivity. The number of genes in the plurality of genes (e.g., at least two) of panel A may be two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, thirty or more, thirty-one or more, thirty-two or more, thirty-three or more, thirty-four or more, thirty-five or more, thirty-six or more, thirty-seven or more, thirty-eight or more, or thirty-nine or more.

Moreover, the methods described herein are useful for diagnosing whether a subject has a receptive endometrial status, a non-receptive endometrial status, a pre-receptive endometrial status, or a post-receptive endometrial status. As used herein, diagnosing includes both diagnosing and aiding in diagnosing. Thus, other diagnostic criteria may be evaluated in conjunction with the results of the methods described herein in order to make a diagnosis.

The disclosure further provides for the communication of the results of the methods described herein to, e.g., technicians, physicians, nurse practitioner or patients. In some embodiments of any of the methods described herein, the method further includes communicating the endometrial status (i.e. as having a receptive endometrial status, as having a non-receptive endometrial status, as having a pre-receptive endometrial status, as having a post-receptive endometrial status) as a report. Any of the methods described herein can include a step of generating or outputting a report providing the results of any of the methods described herein. This report can be provided in the form of a tangible medium (e.g., a report printed on a paper or other tangible medium), in the form of an electronic medium (e.g., an electronic display on a computer monitor), or communicated by phone. In some embodiments, computers are used to communicate results of the methods described herein or predictions, or both, to interested parties, e.g., physicians and their patients.

The methods described herein can be used alone or in combination with other clinical methods for endometrial receptivity stratification known in the art to provide a diagnosis, a prognosis, or a prediction of endometrial receptivity. For example, clinical parameters that are known in the art for predicting endometrial receptivity may be incorporated into the analysis of one of ordinary skill in the art to arrive at an endometrial receptivity assessment with any of the methods described herein.

Methods of Predicting

Also provided herein are methods of predicting endometrial receptivity for embryonic implantation in a human subject that include: (a) providing a first biological sample obtained from a human subject at a first time point within a menstrual cycle; (b) determining the gene expression profile of a panel of genes in the first biological sample, wherein the panel of genes consists of: ANXA4, CATSPERB, PTGFR, PTGS1, IL8, SCGB2A2, ANGPTL1, HPRT1, MMP10, PGR, ITGA8, IFNG, PROK1, FOXO1, CXCL1, STC1, MMP9, MUC1, RPL13A, CALCA, ITGA9, RACGAP1, GPX3, PPP2R2C, ARG2, SCGB3A1, ALDH1A3, APOD, C2CD4B, TFF3, AQP3, GJA4, ARHGDIA, SELL, APOL2, MT1H, MT1X, MT1L, MAOA and MT1F using reverse transcription polymerase chain reaction analysis; and (c) identifying the human subject as having: (i) a receptive endometrial status, wherein the determined gene expression profile corresponds to a gene expression profile of the panel of genes of a receptive endometrial receptivity reference group (ii) a non-receptive endometrial status, wherein the determined gene expression profile corresponds to a gene expression profile of the panel of genes of a non-receptive endometrial reference group, (iii) a pre-receptive endometrial status, wherein the determined gene expression profile corresponds to a gene expression profile of the panel of genes of a pre-receptive endometrial reference group, or (iv) a post-receptive endometrial status, wherein the determined gene expression profile corresponds to a gene expression profile of the panel of genes of a post-receptive endometrial receptivity reference group.

In some aspects, the methods can include transferring pre-implantation embryo into the identified human subject. In other aspects, the methods can include obtaining a second biological sample from the human subject at a second time point and repeating steps (b) and (c) on the second biological sample.

Methods of Determining

As used herein, an endometrial gene expression profile using the selected 40 genes (i.e. panel A) can be determined using any quantitative real-time PCR machine (e.g., a Biomark HD™ System (Fluidigm®)). In some aspects, determining an endometrial gene expression profile of a biological sample (e.g., an endometrial biopsy sample) can include: extracting RNA from the biological sample, performing reverse transcription to generate cDNA, contacting the generated cDNA with pairs of primers targeting the genes of panel A and the control genes, collecting gene expression data using real-time PCR analysis software, performing principal component analysis (PCA) and/or discriminant functional analysis (DA) to determine the endometrial receptivity status of the biological sample as compared to the gene expression profile of panel A of a reference group (e.g., the receptive endometrial reference group, the non-receptive endometrial reference group, the pre-receptive endometrial reference group, the post-receptive endometrial reference group).

Each reverse transcription PCR reaction occurs in a reaction volume that includes all of the components required to carry out a reaction, e.g., primers, buffer, DNA polymerase, reverse transcriptase, sample. The determining step of each gene within the panel of genes is performed in a reaction volume of 0.005 µL to 100 µL (e.g., 0.005 µL, to 100 µL, 0.005 µL, to 90 µL, 0.005 µL to 80 µL, 0.005 µL to 70 µL, 0.005 µL, to 60 µL, 0.005 µL, to 50 µL, 0.005 µL, to 40 µL, 0.005 µL to 30 µL, 0.005 µL, to 20 µL, 0.005 µL to 10 µL, 0.01 µL to 100 µL, 0.01 µL, to 90 µL, 0.01 µL, to 80 µL, 0.01 µL to 70 µL, 0.01 µL to 60 µL, 0.01 µL to 50 µL, 0.01 µL to 40 µL, 0.01 µL to 30 µL, 0.01 µL to 20 µL, 0.01 µL to 10 µL, 0.02 µL to 100 µL, 0.02 µL to 90 µL, 0.02 µL to 80 µL, 0.02 µL to 70 µL, 0.02 µL to 60 µL, 0.02 to 50 µL, 0.02 to 40 µL, 0.02 µL to 30 µL, 0.02 µL to 20 µL, 0.02 µL to 10 µL, 0.05 µL to 100 µL, 0.05 µL to 90 µL, 0.05 µL to 80 µL, 0.05 µL to 70 µL, 0.05 µL to 60 µL, 0.05 µL to 50 µL, 0.05 µL to 40 µL, 0.05 µL to 30 µL, 0.05 µL to 20 µL, 0.05 µL to 10 µL, 1 µL to 100 µL, 1 µL to 90 µL, 1 µL to 80 µL, 1 µL to 70 µL, 1 µL to 60 µL, 1 µL to 50 µL, 1 µL to 40 µL, 1 µL to 30 µL, 1 µL to 20 µL, 1 µL to 10 µL, 5 µL to 100 µL, 5 µL to 90 µL, 5 µL to 80 µL, 5 µL to 70 µL, 5 µL to 60 µL, 5 µL to 50 µL, 5 µL to 40 µL, 5 µL to 30 µL, 5 µL to 20 µL, 5 µL to 10 µL, 10 µL to 100 µL, 10 µL to 90 µL, 10 µL to 80 µL, 10 µL to 70 µL, 10 µL to 60 µL, 10 µL to 50 µL, 10 µL to 40 µL, 10 µL to 30 µL, 10 µL to 20 µL, 15 µL to 100 µL, 15 µL to 90 µL, 15 µL to 80 µL, 15 µL to 70 µL, 15 µL to 60 µL, 15 µL to 50 µL, 15 µL to 40 µL, 15 µL to 30 µL, 15 µL to 20 µL, 20 µL to 100 µL, 20 µL to 90 µL, 20 µL to 80 µL, 20 to 70 µL, 20 µL to 60 µL, 20 to 50 µL, 20 to 40 µL, 20 to 30 µL, 50 µL to 100 µL, 50 to 90 µL, 50 to 80 µL, 50 to 70 µL, 50 to 60 µL, 25 µL to 100 µL, 30 µL to 100 µL, 40 µL to 100 µL, 50 µL to 100 µL, 60 µL to 100 µL, 70 µL to 100 µL, 80 µL to 100 µL, 90 µL to 100 µL).

Methods of digesting a tissue sample (e.g., an endometrial biopsy sample) and extracting RNA from a tissue sample are well-known in the art and are described herein.

As used herein, the term "principal component analysis" or "principal component algorithm" refers to a statistical method that uses an orthogonal transformation to convert a set of observations of possibly correlated variables into a set of values of linearly uncorrelated variables called principal components. It finds the principal components of the dataset and transforms the data into a new, lower-dimensional subspace. The principle component, which can be represented by an eigenvector, mathematically corresponds to a direction in the original n-dimensional space, so that the first principal component accounts for as much of the variance in the data as possible, and each succeeding component accounts for as much of the remaining variance as possible.

Principal component analysis (PCA) is a statistical method that uses an orthogonal transformation to convert a set of observations of possibly correlated variables into a set of values of linearly uncorrelated variables called principal components. It finds the principal components of the dataset and transforms the data into a new, lower-dimensional subspace. The transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables.

Mathematically, the principal components are the eigenvectors of the covariance or correlation matrix of the original dataset. As the covariance matrix or correlation matrix is symmetric, the eigenvectors are orthogonal. The principal components (eigenvectors) correspond to the direction (in the original n-dimensional space) with the greatest variance in the data. Each eigenvector has a corresponding eigenvalue. An eigenvalue is a scalar. The corresponding eigenvalue is a number that indicates how much variance there is in the data along that eigenvector (or principal component). A large eigenvalue means that that principal component explains a large amount of the variance in the data. Similarly, a principal component with a very small eigenvalue explains a small amount variance in the data.

Detailed descriptions regarding how to perform PCA are described in numerous references, e.g., Smith, Lindsay I. "A tutorial on principal components analysis." Cornell University, USA 51 (2002): 52; Shlens, Jonathon. "A tutorial on principal component analysis." arXiv preprint arXiv: 1404.1100 (2014), each of which is incorporated by reference in its entirety.

To apply principle component analysis for the disclosed methods, a set of data comprising expression profile of a panel of genes is created for each sample. The set of data for a sample can be represented by a vector. The dataset can include the expression profile for all subjects in reference group of interest (e.g., a receptive endometrial reference group, a non-receptive endometrial reference group, a pre-receptive endometrial reference group, a post-receptive endometrial reference group) and/or the expression profile of the panel of the genes for tested subjects. The principal component analysis (PCA) converts the dataset into a dataset with lower dimensions. The positions of the each subject (including subjects in the reference group and the tested subject) are determined in this lower dimensional space. In this lower dimension space, if the tested subject is closer to, or is clustered with a particular reference group, then it can be determined that this tested subject corresponds to this particular reference group.

The methods to determine whether a test subject is closer to, or is clustered with, a particular reference group are known in the art, and can be determined by algorithms known in the art, e.g., hierarchical clustering algorithm, k-means clustering algorithm, a statistical distribution model, etc. Various computer algorithms for data analysis and classification are known in the art to compare gene expression profiles. See, e.g., Diaz-Gimeno et al., *Fertil Steril* 2011 95(1): 50-60; Diaz-Gimeno et al., *Fertil Steril* 2013; 99: 508-517.

Kits

Also provided herein are kits that include any of the reagents suitable for predicting endometrial receptivity for transplantation of a pre-implantation embryo. The kits include reagents suitable for determining an endometrial gene expression profile of a panel of genes (e.g., panel A). In some embodiments, the kits can include instructions for performing use of the kit in the methods described herein. In some embodiments, the reagents suitable for determining the endometrial gene expression profile of the biological sample are disposed in an array, a chip, a multi-well plate (e.g., a 96-well plate or a 384-well plate), or a tube (e.g., a 0.2 mL microcentrifuge tube). In some embodiments of any of the kits described herein, the kit includes an array, a chip, a multi-well plate (e.g., a 96-well plate or a 384-well plate), or a tube (e.g., a 0.2 mL microcentrifuge tube). In some embodiments of any of the kits described herein, the kit includes one or more reference groups (e.g., the receptive endometrial reference group, the non-receptive endometrial reference group, the pre-receptive endometrial reference group, the post-receptive endometrial reference group) for determining endometrial gene expression profile of a sample based on computer-assisted algorithms (e.g., principle component analysis, or any other classification algorithms known in the art). In some cases, the kits include software useful for comparing the endometrial gene expression profile of a sample with a reference group (e.g., a prediction model). The software may be provided in a computer readable format (e.g., a compact disc, DVD, flash drive, zip drive etc.), or the software may be available for downloading via the internet. The kits described herein are not so limited; other variations will be apparent to one of ordinary skill in the art.

EXAMPLES

The invention is further described in the following examples, which do not limit the scope of the invention described in the claims.

Example 1. Endometrial Receptivity Testing on Biomark HD™ System (Fluidigm®)

Study Design

In order to define the method for endometrial receptivity evaluation, gene expression data from endometrial biopsies obtained at different moments of the menstrual cycle from healthy fertile donors (group A) and subfertile women (group B) were analyzed. Endometrial biopsies from group A were used to define endometrial receptivity transcriptomic signature. Endometrial samples from group B were tested and diagnosed for receptivity according to the methods described herein and the endometrial receptivity array ERA® (Igenomix, Spain). Receptivity status concordance between the present method and ERA classification was evaluated in this group of samples.

Patient Selection and Sample Collection

Group A consisted of 96 healthy fertile donors (aged between 18 and 34 years), with regular menstrual cycles and normal body mass indicator (BMI) (25-30). Endometrial biopsies from this group were obtained on two different days of the same natural menstrual cycle: LH+2, i.e. two days after the luteinizing hormone (LH) surge and LH+7, i.e. 7 days after the LH surge. Group B consisted of 120 subfertile patients (aged 30-42 years) seeking ART treatment and undergoing hormone replacement (HRT) cycles. Endometrial biopsies from this group of patients were obtained after 5 full days of progesterone impregnation ($P_4$+5).

Endometrial biopsies were obtained from the uterine fundus using a Pipelle catheter (Gynetics, Namont-Achel, Belgium) under sterile conditions. A piece of endometrial tissue of approximately 30 mg was obtained per donor or subfertile patient. The day of the biopsy was calculated in natural cycles as the number of days after the LH surge. The day of the LH surge was considered LH+0. LH urine levels were measured daily using a commercially available detection kit (Clearblue, SPD Swiss Precision Diagnostics; Geneva, Switzerland). In HRT cycles, the day of the biopsy was calculated as the number of days after the first progesterone intake. The day of the first progesterone intake is considered $P_4$+0. After endometrial biopsy collection, tissue was placed in a CryoTube® (Nunc, Roskilde, Denmark) containing 1 ml RNAlater® (Sigma-Aldrich, St Louis, Mo., USA) and stored at −20° C. until further processing. Ethical approval for the study was obtained from Centro Hospital Universitario Virgen del Rocio (Sevilla, Spain, CEI #2014PI/025). All fertile donors and subfertile patients signed an informed consent document.

Reference Genes Selection

Eight candidate reference genes were selected: actin (ACTN), beta-2 microglobulin (B2M), cytochrome C1 (CYC1), EMG1 N1-specific pseudouridine methyltransferase (EMG1), glyceraldehyde-3-phosphate dehydrogenase (GAPDH), TATA-box binding protein (TBP), topoisomerase (DNA) I (TOPI) and tyrosine 3-monooxygenase/tryptophan 5-monooxygenase activation protein zeta (YWHAZ). The expression stability of these reference genes was calculated using the two freeware Microsoft Excel-based applications GeNorm (Vandesompele et al., *Genome Biol* 2002; 3:34-1) and NormFinder (Andersen et al., *Cancer Res* 2004; 64:5245-5250) by following the software developer's manual.

RNA Extraction and cDNA Preparation

Total RNA was extracted using RNeasy mini kit (Qiagen, London, UK) following manufacturer's instructions. RNA purity and concentration was confirmed by NanoDrop 2000 Spectrophotometer (Thermo Scientific, Waltham, Mass., USA) and RNA integrity was assessed using Agilent Bioanalyzer 2100 (Agilent Technologies, Santa Clara, Calif., USA) according to standard protocol provided by the manufacturer. Each total RNA sample was diluted into 250 ng/µl and reverse transcribed into cDNA using Fluidigm® Reverse Transcription Master Mix (Fluidigm®, San Francisco, Calif., USA) following the instructions of the supplier. The cDNA samples were immediately used or stored at −20° C. until further downstream processing for analysis on the BioMark HD™ platform.

Gene Expression Analysis

Pairs of primers targeting the selected and reference genes were designed using the software platform D3 Assay Design (Fluidigm®, San Francisco, Calif.) and obtained from DELTAGene™ (Fluidigm®, San Francisco, Calif.). Specific target amplification (STA) was carried out on cDNA samples using Fluidigm® PreAmp Master Mix and DELTAgene assays (Fluidigm®, San Francisco, Calif.) following the manufacturer's instructions. RT-qPCR reactions were performed following the Fast Gene Expression Analysis Using Evagreen on the Biomark HD™ System, Advanced Development Protocol (PN 100-3488, Rev.C1) (Fluidigm®, San Francisco, Calif.) and 96.96 Dynamic Array™ IFC. The BioMark™ HD System uses microfluidic distribution of samples and requires approximately 7 nL per reaction. Data was collected with Fluidigm® Real-Time PCR analysis software using linear baseline correction method and global auto Cq threshold method. Data were then exported to Excel as .csv files and Cq values normalized using the 3 reference genes included in the analysis.

Principal Component Analysis (PCA) and Discriminant Functional Analysis

Differential expression of genes in the proliferative and secretory phases was assessed by comparing ΔCq values from LH+2 and LH+7 groups. In order to define the genes that had altered mRNA abundance among the groups, a paired t-test (p<0.05) was performed. Fold change (−ΔΔCq) was calculated to determine up-regulated and down regulated genes in the WOI. In order to assess if receptivity status could be established with a reduced number of genes, a principal component analysis (PCA) of the genes showing significant fold change between LH+2 and LH+7 was performed. Discriminant functional analysis (DA) was then used to evaluate the ability of the genes with the highest absolute coefficient value from each of the leading principal components to accurate discriminate samples into the following states: proliferative, receptive, pre-receptive and post-receptive. A Split-Sample validation of the DA was performed to assess the reliability and robustness of discriminant findings. Both fertile and infertile patient samples were split into two subsets. One data set (70% of the samples) was used as a training set and the other one as testing set (remaining 30% of the samples). The percentage of correct classifications was calculated to determine the reliability of the DA model. Data analyses were performed by using IBM SPSS Statistics software version 19.0.

Gene Function Analysis

To study the biological functions and pathways of the genes selected, DAVID v.6.7 bioinformatics resources were used (Huang et al., Nucleic Acids Res 2009; 37:1-13). Assessment and integration of protein-protein interactions was performed by the Search Tool for the Retrieval of Interacting Genes/Proteins (STRING v.10.0 database (Szklarczyk et al., Nucleic Acids Res 2015; 43:D447D452).

Results: Gene Expression, Principal Component Analysis (PCA) and Discriminant Functional Analysis A total of 184 genes related to endometrial receptivity and embryonic implantation were carefully chosen after extensive literature review (Table 1).

TABLE 1

Panel of Selected Genes

| Gene Symbol | Gene Name | Reference | NCBI Accession No. |
| --- | --- | --- | --- |
| ABCC3 | ATP-binding cassette, sub-family C (CFTR/MRP), member 3 | Díaz-Gimeno et al. 2011 | NM_003786.3 |
| ACTA1 | Actin, alpha skeletal muscle | Altmäe et al. 2010 | NM_001100.3 |
| ALDH1A3 | Aldehyde dehydrogenase family 1 member A3 | Dominguez et al. 2009; Haouzi et al 2009, 2013 | NM_000693.3 |
| AMIGO2 | Adhesion molecule with Ig-like domain 2 | Díaz-Gimeno et al. 2011 | NM_001143668.1 |
| ANGPTL1 | Angiopoietin-like 1 | Haouzi et al 2009, 2012 | NM_004673.3 |
| ANXA2 | Annexin A2 | Dominguez et al. 2009; Haouzi et al. 2012; Tracey et al. 2013 | NM_001002857.1 |
| ANXA4 | Annexin A4 | Li et al. 2006; Chen et al 2009; Díaz-Gimeno et al. 2011; Ruíz-Alonso et al. 2012; Haouzi et al. 2012; Tracey et al. 2013 | NM_001153.4 |
| APOD | Apolipoprotein D | Ruíz-Alonso et al. 2012 | NM_001647.3 |
| APOE | Apolipoprotein E | Ruíz-Alonso et al. 2012 | NM_001302688.1 |
| APOL2 | Apolipoprotein L, 2 | Dominguez et al. 2009; Haouzi et al 2009, 2013 | NM_030882.3 |

TABLE 1-continued

Panel of Selected Genes

| Gene Symbol | Gene Name | Reference | NCBI Accession No. |
|---|---|---|---|
| AQP3 | Aquaporin-3 | Díaz-Gimeno et al. 2011; Ruíz-Alonso et al. 2012 | NM_004925.4 |
| AREG | Amphiregulin | Aghajanova et al. 2008; Barnea et al. 2012 | NM_001657.3 |
| ARG2 | Arginase 2 | Díaz-Gimeno et al. 2011 | NM_001172.3 |
| ARHGDIA | Rho GDP-dissociation inhibitor (GDI) alpha | Chen et al. 2009; Tracey et al. 2013 | NM_001185077.2 |
| ATP5B | ATP synthase, H+ transporting, mitochondrial F1 complex, beta polypeptide | Sadek et al. 2012 | NM_001686.3 |
| BTC | Probetacellulin | Barnea et al. 2012 | NM_001729.3 |
| C2CD4B | C2 calcium-dependent domain-containing protein 4B | Haouzi et al. 2009, 2012 | NM_001007595.2 |
| C4BPA | Complement component 4 binding protein, alpha | Díaz-Gimeno et al. 2011 | NM_000715.3 |
| CALCA | Calcitonin-related polypeptide alpha | Otsuka et al., 2007 | NM_001033953.2 |
| CALR | Calreticulin | Parmar et al. 2009; Tracey et al. 2013 | NM_004343.3 |
| CAPN6 | Calpain-6 | Altmäe et al. 2010; Díaz-Gimeno et al. 2011 | NM_014289.3 |
| CATSPERB | Cation channel sperm auxiliary subunit beta | Díaz-Gimeno et al. 2011 | NM_024764.3 |
| CCL2 | Chemokine (C-C motif) ligand 2 | Barnea et al. 2012 | NM_002982.3 |
| CCR7 | Chemokine (C-C motif) receptor 7 | Altmäe et al. 2010 | NM_001838.3 |
| CD55 | CD55 molecule, decay accelerating factor for complement (Cromer blood group) | Ruíz-Alonso et al. 2012 | NM_000574.4 |
| CDA | Cytidine deaminase | Díaz-Gimeno et al. 2011 | NM_001785.2 |
| CDH1 | Cadherin-1, type 1, Epitelial-Cadherin | Banerjee et al. 2013 | NM_004360.4 |
| CIR1 | Corepressor interacting with RBPJ 1 | Ruíz-Alonso et al. 2012 | NM_004882.3 |
| CLDN4 | Claudin-4 | Ruíz-Alonso et al. 2012 | NM_001305.4 |
| CLIC1 | Chloride intracellular channel protein 1 | Chen et al. 2009; Tracey et al. 2013 | NM_001287593.1 |
| CLU | Clusterin | Díaz-Gimeno et al. 2011 | NM_001831.3 |
| CMTM5 | CKLF-like MARVEL transmembrane domain-containing protein 5 | Altmäe et al. 2010 | NM_138460.2 |
| COL16A1 | Collagen, type XVI, alpha 1 | Altmäe et al. 2010; Díaz-Gimeno et al. 2011 | NM_001856.3 |
| CRHR2 | Corticotropin-releasing factor receptor 2 | Makrigianakis et al. 2004 | NM_001883.4 |
| CRISP3 | Cysteine-rich secretory protein 3 | Díaz-Gimeno et al. 2011; Ruíz-Alonso et al. 2012 | NM_006061.3 |

TABLE 1-continued

Panel of Selected Genes

| Gene Symbol | Gene Name | Reference | NCBI Accession No. |
|---|---|---|---|
| CSF1 | Colony stimulating factor 1 (macrophage) | Gargiulo et al. 2004; Aghajanova et al. 2008; Tawfeek et al. 2012 | NM_000757.5 |
| CSF3 | Colony stimulating factor 3 (granulocyte) | Lédée et al. 2011 | NM_000759.3 |
| CSRP2 | Cysteine and glycine-rich protein 2 | Díaz-Gimeno et al. 2011 | NM_001321.2 |
| CTNNA2 | Catenin alpha-2 | Altmäe et al. 2010; Díaz-Gimeno et al. 2011 | NM_001282597.2 |
| CXCL1 | Growth-regulated alpha protein | Barnea et al. 2012 | NM_001511.3 |
| CXCL14 | C—X—C motif chemokine 14 | Díaz-Gimeno et al. 2011; Ruíz-Alonso et al. 2012 | NM_004887.4 |
| CXCL6 | C—X—C motif chemokine 6 (Chemokine alpha 3) | Altmäe et al. 2010 | NM_002993.3 |
| DEFB1 | Beta-defensin 1 | Díaz-Gimeno et al. 2011 | NM_005218.3 |
| DKK1 | Dickkopf WNT signaling pathway inhinitor 11 | Díaz-Gimeno et al. 2011; Ruíz-Alonso et al. 2012 | NM_012242.3 |
| EGF | Epidermal Growth Factor | Gargiulo et al. 2004; Aghajanova et al. 2008; Sing et al. 2011; Barnea et al. 2012 | NM_001963.5 |
| EPHB3 | EPH receptor B3 | Díaz-Gimeno et al. 2011 | NM_004443.3 |
| EREG | Proepiregulin | Barnea et al. 2012 | NM_001432.2 |
| ESR1 | Estrogen receptor 1 | Gao et al. 2012 | NM_000125.3 |
| ESR2 | Estrogen Receptor 2 (ER Beta) | Altmäe et al. 2010 | NM_001437.2 |
| EZR | Ezrin | Chen et al. 2009; Tracey et al. 2013 | NM_003379.4 |
| FAM3B | Family with sequence similarity 3, member B | Altmäe et al. 2010 | NM_058186.3 |
| FAM3D | Family with sequence similarity 3, member D | Altmäe et al. 2010 | NM_138805.2 |
| FASLG | Fas ligand (TNF superfamily, member 6) | Makrigianakis et al. 2004 | NM_000639.2 |
| FGF7 | Fibroblast growth factor 7 | Cavagna et al. 2003 | NM_002009.3 |
| FOXO1 | Forkhead box protein O1 | Ruíz-Alonso et al. 2012 | NM_002015.3 |
| FOXP3 | Forkhead box protein P3 | Chen et al. 2012 | NM_014009.3 |
| FUT4 | Fucosyltransferase 4 (alpha (1,3) fucosyltransferase, myeloid-specific | Liu et al. 2012 | NM_002033.3 |
| FZD5 | Frizzled-5 | Liu et al. 2010 | NM_003468.3 |
| GABARAPL1 | Gamma-aminobutyric acid (GABA(A) receptor-associated protein-like 1 | Díaz-Gimeno et al. 2011 | NM_031412.2 |
| GADD45A | Growth arrest and DNA damage-inducible protein GADD45 alpha | Díaz-Gimeno et al. 2011; Ruíz-Alonso et al. 2012 | NM_001924.3 |
| GAST | Gastrin | Díaz-Gimeno et al. 2011 | NM_000805.4 |
| GDF15 | Growth differentiation factor 15 | Díaz-Gimeno et al. 2011 | NM_004864.3 |

TABLE 1-continued

Panel of Selected Genes

| Gene Symbol | Gene Name | Reference | NCBI Accession No. |
|---|---|---|---|
| GJA4 | Gap junction protein, alpha 4, 37 kDa | Ruíz-Alonso et al. 2012 | NM_002060.2 |
| GNLY | Granulysin | Díaz-Gimeno et al. 2011; Ruíz-Alonso et al. 2012 | NM_001302758.1 |
| GPX3 | Glutathione peroxidase 3 | Díaz-Gimeno et al. 2011; Ruíz-Alonso et al. 2012 | NM_002084.4 |
| HBA1 | Hemoglobin, alpha 1 | Altmäe et al. 2010 | NM_000558.4 |
| HBEGF | Heparin Binding-EGF-like growth factor | Stavreus-Evers et al. 2002; Aghajanova et al. 2008; Altmäe et al. 2010; Sing et al. 2011; Barnea et al. 2012 | NM_001945.2 |
| HBG1 | Hemoglobin, gamma A | Altmäe et al. 2010 | NM_000559.2 |
| HMBS | Hydroxymethylbilane synthase | Vestergaard et al. 2011 | NM_000190.3 |
| HOXA10 | Homeobox A10 | Aghajanova et al. 2008; Wei et al. 2009; Kakmak et al. 2011; Ruíz-Alonso et al. 2012; Garrido-Gómez et al. 2013; Jana et al. 2013 | NM_018951.3 |
| HOXA11 | Homeobox A11 | Lynch et al., 2009 | NM_005523.5 |
| HOXB7 | Homeobox B7 | Ruíz-Alonso et al. 2012 | NM_004502.3 |
| HPRT1 | Hypoxanthine phosphoribosyltransferase 1 | Vestergaard et al. 2011 | NM_000194.2 |
| HPSE | Heparanase | Díaz-Gimeno et al. 2011 | NM_006665.5 |
| ICAM1 | Intercellular adhesion molecule 1 | Zhao et al., 2010 | NM_000201.2 |
| ID4 | DNA-binding protein inhibitor ID-4 | Díaz-Gimeno et al. 2011; Ruíz-Alonso et al. 2012 | NM_001546.3 |
| IDH1 | Isocitrate dehydrogenase 1 (NADP+), soluble | Díaz-Gimeno et al. 2011 | NM_005896.3 |
| IER3 | Immediate early response 3 | Díaz-Gimeno et al. 2011 | NM_003897.3 |
| IFNG | Interferon gamma | Banerjee et al. 2013 | NM_000619.2 |
| IGFBP1 | Insulin-like growth factor-binding protein 1 | Altmäe et al. 2010; Díaz-Gimeno et al. 2011 | NM_000596.3 |
| IGFBP3 | Insulin-like growth factor-binding protein 3 | Ruíz-Alonso et al. 2012 | NM_001013398.1 |
| IL10 | Interleukin 10 | Banerjee et al. 2013 | NM_000572.2 |
| IL11 | Interleukin 11 | Altmäe et al. 2010; Sing et al. 2011; Tawfeek et al. 2012 | NM_000641.3 |

TABLE 1-continued

Panel of Selected Genes

| Gene Symbol | Gene Name | Reference | NCBI Accession No. |
|---|---|---|---|
| IL15 | Interleukin-15 | Lédée et al. 2011; Díaz-Gimeno et al. 2011; Ruíz-Alonso et al. 2012 | NM_000585.4 |
| IL18 | Interleukin-18 | Lédée et al. 2011 | NM_001562.3 |
| IL1B | Interleukin 1 Beta | Gargiulo et al. 2004; Aghajanova et al. 2008; Altmäe et al. 2010; Cheong et al. 2012; Koot et al. 2012; Banerjee et al. 2013 | NM_000576.2 |
| IL1R1 | Interleukin-1 Receptor type | Garrido-Gómez et al. 2013 | NM_001288706.1 |
| IL2 | Interleukin 2 | Banerjee et al. 2013 | NM_000586.3 |
| IL21 | Interleukin-21 | Altmäe et al. 2010 | NM_021803.3 |
| IL4 | Interleukin 4 | Banerjee et al. 2013 | NM_000589.3 |
| IL5 | Interleukin 5 (colony-stimulating factor, eosinophil) | Teklenburg et al., 2010 | NM_000879.2 |
| IL6 | Interleukin 6 | Sing et al. 2011; Cheong et al. 2012; Koot et al. 2012; Barnea et al. 2012; Tawfeek et al. 2012 | NM_000600.4 |
| IL8 | Interleukin 8 | Banerjee et al. 2013 | NM_000584.3 |
| ITGAV | Integrin, alpha V | Lessey et al., 2000; Nardo et al. 2003; Aghajanova et al. 2008; Barnea et al. 2012; Ruíz-Alonso et al. 2012; Koot et al. 2012; Jana et al. 2013; Tracey et al. 2013 | NM_002210.4 |
| ITGA2 | Integrin, alpha 2 (CD49B, alpha 2 subunit of VLA-2 receptor) | Barnea et al. 2012 | NM_002203.3 |
| ITGA8 | Integrin, alpha 8 | Altmäe et al. 2010 | NM_003638.2 |
| ITGA9 | Integrin, alpha 9 | Barnea et al. 2012 | NM_002207.2 |
| ITGB1 | Integrin, beta 1 | Barnea et al. 2012 | NM_002211.3 |
| ITGB3 | Integrin, beta 3 | Barnea et al. 2012 | NM_000212.2 |
| KCNG1 | Potassium voltage-gated channel subfamily G member 1 | Díaz-Gimeno et al. 2011 | NM_002237.3 |
| LCP1 | Lymphocyte cytosolic protein (L-plastin) | Dominguez et al. 2009; Haouzi et al. 2009, 2013 | NM_002298.4 |

TABLE 1-continued

Panel of Selected Genes

| Gene Symbol | Gene Name | Reference | NCBI Accession No. |
|---|---|---|---|
| LEP | Leptin | Labarta et al., 2011 | NM_000230.2 |
| LIF | Leukaemia Inhibitor Factor | Aghajanova et al. 2003; Gargiulo et al. 2004; Aghajanova et al. 2008; Altmäe et al. 2010; Sing et al. 2011; Díaz-Gimeno et al. 2011; Tawfeek et al. 2012; Ruíz-Alonso et al. 2012; Tawfeek et al. 2012; Jana et al. 2013; Garrido-Gómez et al. 2013 | NM_002309.4 |
| LIFR | Leukemia inhibitory factor Receptor alpha | Aghajanova et al. 2003; Aghajanova et al. 2008; Tawfeek et al. 2012 | NM_001127671.1 |
| LPAR3 | Lysophosphatidic acid receptor 3 | Wei et al. 2009 | NM_012152.2 |
| LRPPRC | Leucine-rich PPR motif-containing protein | Tawfeek et al., 2012; Tracey et al. 2013 | NM_133259.3 |
| LRRC17 | Leucine-rich repeat-containing protein 17 | Díaz-Gimeno et al. 2011 | NM_001031692.2 |
| LYPD3 | Ly6/PLAUR domain-containing protein 3 | Díaz-Gimeno et al. 2011 | NM_014400.2 |
| MAOA | Monoamine oxidase A | Dominguez et al. 2009; Díaz-Gimeno et al. 2011; Ruíz-Alonso et al. 2012; Haouzi et al. 2012 | NM_000240.3 |
| MAP2K1 | Mitogen-activated protein kinase 1 | Barnea et al. 2012 | NM_002755.3 |
| MAP3K5 | Mitogen-activated protein kinase 5 | Ruíz-Alonso et al. 2012 | NM_005923.3 |
| MAPK1 | Mitogen-activated protein kinase 1 | Barnea et al. 2012 | NM_002745.4 |
| MAPK3 | Mitogen-activated protein kinase 3 | Barnea et al. 2012 | NM_002746.2 |
| MAPK8 | Mitogen-activated protein kinase 8 | Barnea et al. 2012 | NM_001278547.1 |
| MFAP5 | Microfibrillar-associated protein 5 | Haouzi et al. 2009, 2012; Díaz-Gimeno et al. 2011 | NM_003480.3 |
| MMP10 | Matrix metallopeptidase 10 (Stromelysin-2) | Altmäe et al. 2010 | NM_002425.2 |
| MMP2 | Matrix Metalloproteinase 2 (gelatinase A, 72 kDA gelatinase, 72 kDA type IV collagenase) | Banerjee et al. 2013 | NM_004530.5 |
| MMP26 | Matrix metallopeptidase 26 | Altmäe et al. 2010; Ruíz-Alonso et al. 2012 | NM_021801.4 |

TABLE 1-continued

Panel of Selected Genes

| Gene Symbol | Gene Name | Reference | NCBI Accession No. |
|---|---|---|---|
| MMP8 | Matrix metallopeptidase 8 (Neutrophil collagenase) | Altmäe et al. 2010 | NM_002424.2 |
| MMP9 | Matrix Metallopeptidase9 (gelatinase B, 92 kDa gelatinase, 92 kDa type IV collagenase) | Banerjee et al. 2013 | NM_004994.2 |
| MT1E | Metallothionein 1E | Ruíz-Alonso et al. 2012 | NM_175617.3 |
| MT1F | Metallothionein 1F | Ruíz-Alonso et al. 2012 | NM_005949.3 |
| MT1G | Metallothionein 1G | Díaz-Gimeno et al. 2011; Ruíz-Alonso et al. 2012 | NM_001301267.1 |
| MT1H | Metallothionein 1H | Ruíz-Alonso et al. 2012 | NM_005951.2 |
| MT1L | Metallothionein 1L | Ruíz-Alonso et al. 2012 | NR_001447.2 |
| MT1X | Metallothionein 1X | Ruíz-Alonso et al. 2012 | NM_005952.3 |
| MT2A | Metallothionein 2 | Díaz-Gimeno et al. 2011; Ruíz-Alonso et al. 2012 | NM_005953.4 |
| MUC1 | Mucin 1, cell surface associated | Altmäe et al. 2010; Koot et al. 2012; Garrido-Gómez et al. 2013 | NM_002456.5 |
| MUC16 | Mucin-16, cell surface associated | Altmäe et al. 2010; Díaz-Gimeno et al. 2011 | NM_024690.2 |
| MUC4 | Mucin-4, cell surface associated | Aghajanova et al. 2008; Altmäe et al. 2010 | NM_018406.6 |
| MUC5B | Mucin-5B, oligomeric mucus/gel-forming | Aghajanova et al. 2008; Altmäe et al. 2010 | NM_002458.2 |
| NFKB1 | Nuclear factor of kappa light polypeptide enhancer in B cells 1 | Barnea et al. 2012 | NM_003998.3 |
| NFKBIA | Nuclear factor of kappa light polypeptide enhancer in B cells inhibitor, alpha | Barnea et al. 2012 | NM_020529.2 |
| NFKBIE | Nuclear factor of kappa light polypeptide enhancer in B cells inhibitor, epsilon | Barnea et al. 2012 | NM_004556.2 |
| NNMT | Nicotinamide N-methyltransferase | Díaz-Gimeno et al. 2011 | NM_006169.2 |
| OPRK1 | Opiod receptor, kappa 1 | Díaz-Gimeno et al. 2011 | NM_000912.4 |
| PAEP | Progestagen-associated endometrial protein | Stavreus-Evers et al. 2006; Aghajanova et al. 2008; Wei et al. 2009; Díaz-Gimeno et al. 2011, Ruíz-Alonso et al. 2012; Ming-Qing et al. 2013 | NM_001018049.2 |

TABLE 1-continued

Panel of Selected Genes

| Gene Symbol | Gene Name | Reference | NCBI Accession No. |
|---|---|---|---|
| PGR | Progesterone Receptor | Stavreus-Evers et al. 2001; Aghajanova et al. 2008; Gao et al. 2012 | NM_000926.4 |
| PGRMC1 | Progesterone receptor membrane component 1 | Chen et al. 2009; Tracey et al. 2013 | NM_006667.4 |
| PLA2G16 | Phospholipase A2, group XVI | Díaz-Gimeno et al. 2011 | NM_007069.3 |
| PLA2G4A | Phospholipase A2, group IVA (cytosolic, calcium-dependent) | Berlanga et al. 2011 | NM_024420.2 |
| PPP2R2C | Protein phosphatase 2, regulatory subunit B, gamma | Barnea et al. 2012 | NM_020416.3 |
| PRDX1 | Peroxiredoxin 1 | Stavreus-Evers et al. 2002; Aghajanova et al. 2008 | NM_002574.3 |
| PRDX2 | (Peroxiredoxin 2 | Stavreus-Evers et al. 2002; Aghajanova et al. 2008 | NM_005809.5 |
| PRKCG | Protein kinase C, gamma | Altmäe et al. 2010 | NM_001316329.1 |
| PROK1 | Prokineticin-1 | Haouzi et al 2009, 2012 | NM_032414.2 |
| PTGER3 | Prostaglandin E receptor 3 (subtype EP3) | Banerjee et al. 2013; Vilella et al. 2013 | NM_001126044.1 |
| PTGFR | Prostaglandin F receptor (FP) | Berlanga et al. 2011 | NM_000959.3 |
| PTGS1 | Prostaglandin-endoperoxide synthase 1 (prostaglandin G/H synthase and cyclooxygenase) | Aghajanova et al. 2008; Sing et al. 2011; Koot et al. 2012 | NM_000962.3 |
| PTGS2 | Prostaglandin-endoperoxide synthase 2 (prostaglandin G/H synthase and cyclooxygenase) | Aghajanova et al. 2008; Sing et al. 2011; Koot et al. 2012; Banerjee et al. 2013 | NM_000963.3 |
| PTPRZ1 | Protein-tyrosine phosphatase, receptor type, Z polypeptide 1 | Barnea et al. 2012 | NM_002851.2 |
| RAC1 | Ras-related C3 botulinum toxin substrate 1 (rho family, small GTP binding protein Rac1) | Grewal et al., 2008 | NM_018890.3 |
| RACGAP1 | Rac GTPase-activating protein 1 | Grewal el al. 2008 | NM_013277.4 |
| RHOA | Ras homolog family member A | Heneweer et al., 2008 | NM_001664.3 |
| RPL13A | Ribosomal protein L13a | Vestergaard et al. 2011 | NM_012423.3 |
| S100A1 | S100 calcium binding protein A1 | Díaz-Gimeno et al. 2011 | NM_006271.1 |
| S100A10 | S100 calcium binding protein A10 | Dominguez et al. 2009; Haouzi et al 2009, 2013; Ruiz-Alonso et al. 2013 | NM_002966.2 |

TABLE 1-continued

Panel of Selected Genes

| Gene Symbol | Gene Name | Reference | NCBI Accession No. |
| --- | --- | --- | --- |
| S100A2 | S100 calcium binding protein A2 | Altmäe et al. 2010 | NM_005978.3 |
| S100P | S100 calcium binding protein P | Díaz-Gimeno et al. 2011; Zhang et al. 2012 | NM_005980.2 |
| SCGB2A2 | Secretoglobin, family 2A, member 2 | Díaz-Gimeno et al. 2011 | NM_002411.3 |
| SCGB3A1 | Secretoglobin, family 3A, member 1 | Altmäe et al. 2010 | NM_052863.2 |
| SDHA | Succinate dehydrogenase complex, subunit A, flavoprotein (Fp) | Vestergaard et al. 2011; Sadek et al. 2012 | NM_004168.3 |
| SELL | Selectin L | Genbaced et al. 2003; Aghajanova et al. 2008; Ruíz-Alonso et al. 2012; Banerjee et al. 2013 | NM_000655.4 |
| SERPINA1 | Serpin peptidase inhibitor, clade A (alpha-1 antiproteinase, antitrypsin), member 1 | Parmar et al. 2009; Tracey et al. 2013 | NM_000295.4 |
| SERPING1 | Serpin peptidase inhibitor, clade G (C1 inhibitor), member 1 | Díaz-Gimeno et al. 2011; Ruíz-Alonso et al. 2012 | NM_000062.2 |
| SGK1 | Serine/glucocorticoid regulated kinase 1 | Altmäe et al. 2010 | NM_005627.3 |
| SLPI | Secretory leukocyte peptidase inhibitor | Díaz-Gimeno et al. 2011 | NM_003064.3 |
| SOD2 | Superoxide dismutase 2, mitochondrial | Díaz-Gimeno et al. 2011 | NM_000636.3 |
| SPDEF | SAM pointed domain containing ETS transcription factor | Díaz-Gimeno et al. 2011 | NM_012391.2 |
| SPP1 | Secreted phosphoprotein 1 (Osteopontin) | Lessey et al. 2003; Aghajanova et al. 2008; Wei et al. 2009; Díaz-Gimeno et al. 2011; Barnea et al. 2012; Ruíz-Alonso et al. 2012, Garrido-Gómez et al. 2013 | NM_001251830.1 |
| STAT3 | Signal transducer and activator of transcription 3 (Acute-phase response factor) | Catalano et al. 2005 | NM_139276.2 |
| STC1 | Stanniocalcin-1 | Ruíz-Alonso et al. 2012 | NM_003155.2 |
| STMN1 | Stathmin 1 | Chen et al. 2009; Dominguez et al. 2009; Haouzi et al. 2012; Tracey et al. 2013 | NM_001145454.2 |
| TAGLN2 | Transgelin 2 | Dominguez et al. 2009; Haouzi et al 2009, 2013; Díaz-Gimeno et al. 2011 | NM_001277224.1 |

TABLE 1-continued

Panel of Selected Genes

| Gene Symbol | Gene Name | Reference | NCBI Accession No. |
|---|---|---|---|
| TFF3 | Trefoil factor 3 (intestinal) | Altmäe et al. 2010; Ruiz-Alonso et al. 2012 | NM_003226.3 |
| TGFB1 | Transforming growth factor, beta 1 | Gargiulo et al. 2004; Aghajanova et al. 2008; Sing et al. 2011; Barnea et al. 2012; Banerjee et al. 2013 | NM_000660.6 |
| TNC | Tenascin | Barnea et al. 2012 | NM_002160.3 |
| TNF | Tumor Necrosis Factor alpha | Banerjee et al. 2013 | NM_000594.3 |
| TNFRSF11B | Tumor necrosis factor receptor superfamily, member 11B | Barnea et al. 2012 | NM_002546.3 |
| TSPAN8 | Tetraspanin 8 | Díaz-Gimeno et al. 2011 | NM_004616.2 |
| VCAM1 | Vascular cell adhesion protein 1 | Díaz-Gimeno et al. 2011; Barnea et al. 2012 | NM_001078.3 |
| VEGFA | Vascular Endothelial Growth Factor A | Banerjee et al. 2013 | NM_001025366.2 |
| WISP2 | WNT1-inducible-signaling pathway protein 2 | Altmäe et al. 2010 | NM_001323370.1 |

Several biological processes mainly related to cellular proliferation, response to wounding, defense and immune response were found to be statistically over-represented as analyzed by DAVID bioinformatics tool (Table 2).

TABLE 2

GO functional enrichment of the 192 WO1 genes

| Category | Term | Genes | % | p-value |
|---|---|---|---|---|
| BP | Regulation of cell proliferation | 47 | 24.6 | 9.0E−19 |
| BP | Positive regulation of cell proliferation | 33 | 17.3 | 1.6E−16 |
| BP | Response to wounding | 35 | 18.3 | 5.1E−15 |
| BP | Defense response | 36 | 18.8 | 6.8E−14 |
| BP | Positive regulation of immune system process | 23 | 12.0 | 3.9E−13 |
| BP | Negative regulation of transport | 18 | 9.4 | 1.4E−12 |
| MF | Cytokine activity | 30 | 15.7 | 3.7E−23 |
| MF | Growth factor activity | 23 | 12.0 | 6.0E−17 |
| MF | Cadmium ion binding | 5 | 2.6 | 4.9E−6 |
| MF | Antioxidant activity | 7 | 3.7 | 2.6E−5 |
| CC | Extracellular region part | 65 | 34 | 6.3E−30 |
| CC | Extracellular space | 55 | 28.8 | 2.0E−28 |

BP = biological process,
MF = molecular function;
CC = cellular component

Exploration of the interactions of proteins codified by the selected genes rendered the following results: a total of 1,334 protein-protein interactions when the expected was 425 in the network analysis (clustering coefficient=0.616) (FIG. 1). The set of proteins codified by the selected genes have more interactions among themselves than what would be expected for a random set of proteins of similar size, drawn from the genome. Such enrichment indicated that these proteins were biologically connected as a group.

Expression stability analysis of the eight selected reference genes showed that Cytochrome C1 (CYC1), glyceraldehyde-3-phosphate dehydrogenase (GAPDH), TATA-box binding protein (TBP) and tyrosine 3-monooxygenase/tryptophan 5-monooxygenase activation protein zeta (YWHAZ) were the most stable genes. These genes, previously found to be useful for normalizing endometrial gene expression data (Vestergaard et al., *Mol Hum Reprod* 2011; 17:243-254; Sadek et al., *Hum Reprod* 2012; 27:251-256), and were selected and used for normalization of gene expression values.

Figure 2A:
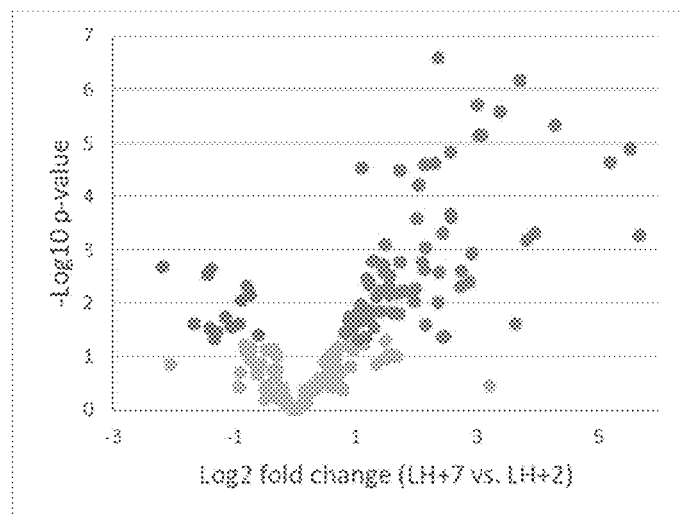
FIG. 2A is a representative volcano plot of gene expression differences for the 184 WOI genes on days LH+2 and LH+7 of fertile subjects menstrual cycles. The log 2 fold change is plotted on the x-axis and the negative log 10 p-value is plotted on the y-axis. Green dots represent gene probes with P value <0.05 by paired t-test and downregulated fold change (log 2FC<−0.5). Orange dots represent gene probes with p-value <0.05 by paired t-test and up-regulated fold change (log 2FC>0.5).
Figure 2B:
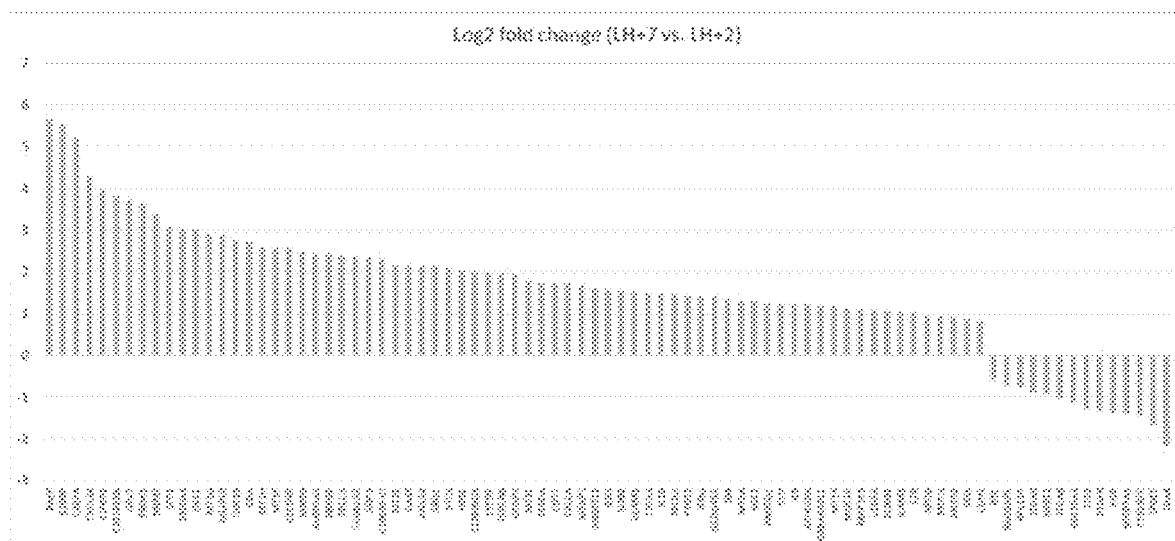
FIG. 2B is a representative bar graph showing log 2 fold changes of the 85 differentially expressed mRNAs (Paired t-test, p<0.05) in LH+7 vs LH+2. 71 mRNAs were upregulated and 14 mRNAs were downregulated in LH+7 compared to LH+2.

Comparison of gene expression data of the selected WOI genes in fertile subjects on days LH+2 and LH+7 of their cycles showed a total of 85 genes presenting significant differences in the fold change (p<0.05; paired t-test) between the proliferative (LH+2) and the secretory phase (LH+7). Most genes were up regulated (n=71) rather than downregulated (n=14) (FIGS. 2A and 2B). Gene ontology (GO) analysis revealed that these 85 genes were related to cell division and proliferation, cell signaling and response, extracellular organization and communication, immunological activity, vascular proliferation, blood pressure regulation and embryo implantation. Additionally, comprehensive analysis of protein-protein interactions showed a total of 23 interactions when the expected number was 10 (clustering coefficient=0.218, P=0.000344).

Figure 3A:
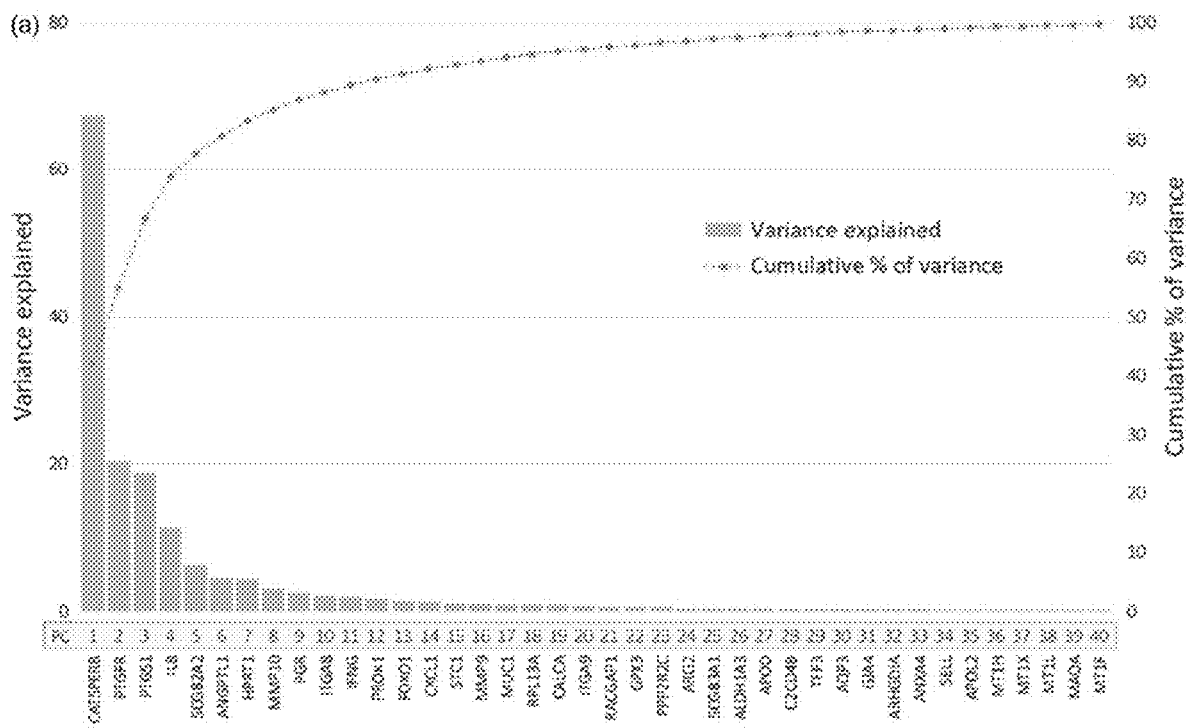
FIG. 3A is a representative chart for the variance (eigenvalue) provided by each principal component (PC) from the PCA and the cumulative percentage along the 40 PCs. The green bars illustrate the variance of each PC, and the orange line illustrates the cumulative variance explained by the retaining PCs. The genes with the highest coefficient value from each component are detailed below each PC number.
Figure 3B:
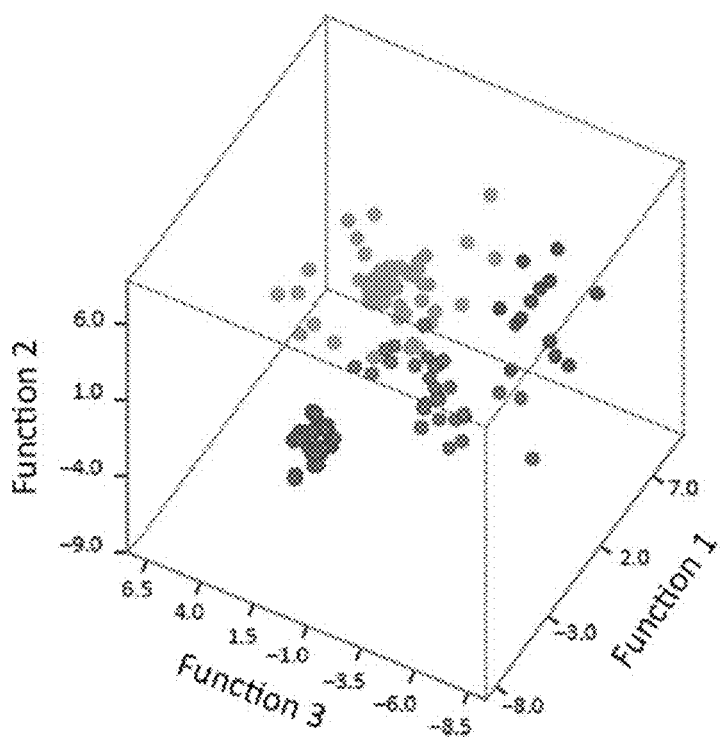
FIG. 3B is a representative canonical plot using discriminant functional analysis with the 40 genes selected to classify 312 endometrial samples. X, Y and Z axis represent the discriminant function scores for the first three dimensions. Non-receptive samples are represented as blue circle, pre-receptive as green circle, receptive as orange circle and post-receptive as purple circle.

Principal component analysis (PCA) of the 85 genes showing significant fold change between LH+2 and LH+7 revealed that 40 components explained more than 99.5% of total sample variance. The variance provided by each component and the cumulative percentage along the 40 components together with the genes with the highest absolute coefficient value from each of the leading principal components are represented in FIG. 3A. These genes were selected for further discriminant function analysis (DA) (Jolliffe *Appl Stat* 1972; 21:160-173; Jolliffe *Applied Stat* 1973; 22:21-31). DA assessed the effectiveness of the selected genes to accurately classify the receptivity status of endometrial biopsies from both fertile donors and subfertile patients (FIG. 3B).

Within the group of donors, the selected 40 genes disclosed in FIG. 3A (endometrial receptivity panel A genes) allowed accurate classification of samples into two endometrial receptivity statuses: proliferative (non-receptive) and receptive. Using a DA model based on the 40 genes selected, 100% of LH+2 samples were categorised as non-receptive, and all LH+7 samples were classified as receptive in both the training and test sets (Table 3).

TABLE 3

Discriminant Functional Analysis Classification Results

|  | ORIGINAL GROUP MEMBERSHIP | N | PREDICTED GROUP MEMBERSHIP (%)$^{a,b,c,d}$ | | | |
|---|---|---|---|---|---|---|
|  |  |  | Non-receptive | Pre-receptive | Receptive | Post-receptive |
| DONORS | | | | | | |
| Training Set | LH + 2 | 67 | 100.0 | — | 0.0 | — |
|  | LH + 7 | 67 | 0.0 | — | 100.0 | — |
| Test Set | LH + 2 | 29 | 100.0 | — | 0.0 | — |
|  | LH + 7 | 29 | 0.0 | — | 100.0 | — |
| PATIENTS | | | | | | |
| Training Set | Pre-receptive | 29 | — | 100.0 | 0.0 | 0.0 |
|  | Receptive | 41 | — | 2.4 | 95.1 | 2.4 |
|  | Post-receptive | 13 | — | 0.0 | 0.0 | 100.0 |
| Test Set | Pre-receptive | 13 | — | 92.3 | 7.7 | 0.0 |
|  | Receptive | 18 | — | 5.6 | 94.4 | 0.0 |
|  | Post-receptive | 6 | — | 0.0 | 16.7 | 83.3 |

$^a$Donors training set: 100% of original grouped cases correctly classified
$^b$Donors testing set: 100% of original grouped cases correctly classified
$^c$Patients training set: 97.59% of original grouped cases correctly classified
$^d$Patients testing set: 91.67% of original grouped cases correctly classified Within the patient group, the endometrial receptivity panel A genes classification matched the endometrial biopsy status prediction provided by an independent endometrial receptivity test (ERA) in 97.59% samples in the training set and 91.67% in the testing set. In the training set, two samples were classified differently by the two tests and, in the testing set, there were three.

The accurate identification of the period of endometrial receptivity could be key for the achievement of a successful pregnancy in many couples. The importance of embryonic-endometrial synchrony for successful implantation have been reported in several studies. Shapiro et al. (2008) showed that the lower implantation rates observed in Day 6 embryos transferred fresh compared to Day 5 embryos were not due to an embryonic factor but rather to the endometrial moment where embryos were transferred. No differences in implantation rates were detected in cryotransfers of either day 5 or day 6 blastocysts. Similar results were reported by Franasiak et al. (2013) that showed that the diminished ART outcomes from embryos with delayed blastulation, traditionally attributed to reduced embryo quality, result from an embryonic-endometrial dissynchrony. These studies highlight the importance of embryo-endometrial synchrony to increase implantation rates.

Reports exploring the concept of the WOI, show that the timing of implantation can also influence pregnancy loss. Wilcox et al. (1999) showed a strong increase in the risk of early pregnancy loss with late implantation. Further studies looking at the impact of endometrial-embryo asynchrony on ART outcomes have found that the combination of elevated progesterone on the day of trigger (advanced endometrium) and slow growing embryos results in low live birth rates (Healy et al., *Hum Reprod* 2017; 32:362-367). This problem seems to be influenced by maternal age. Shapiro et al. in a recent study (2016) reported elevated incidence of factors associated with embryo-endometrium asynchrony in women over 35 years, high pre-ovulatory serum progesterone levels and increased numbers of delayed-growth embryos. This, together with the already well known decrease in gamete quality of women of advanced reproductive age (Fragouli et al., *Hum Genet* 2013; 132:1001-1013), underlines the importance of women's age for reproductive success and the need for the development of diagnostic and therapeutic tools to increase the chances of these women becoming a mother.

In contrast to previous studies aimed at developing tools for endometrial receptivity evaluation (Horcajadas et al., *Fertil Steril* 2008; 88:S43-S44; Diaz-Gimeno et al., *Fertil Steril* 2011; 95: 50-60, 60-15), a selection of genes was chosen which are involved in biological processes taking place on the endometrium during the WOI and which are related to endometrial preparation for embryonic implantation. Upon the selection performed based on the literature, an over-representation of processes very relevant to the phenomenon of endometrial receptivity acquisition such as cellular proliferation, response to wounding, defense and immune response, were found. Within this group of genes, a subset of 85 especially were found to be interesting as they showed significant differences in expression between the proliferative and secretory phases. These genes GO analyses revealed cellular components, biological processes and molecular functions related to cell signaling and response, extracellular organization, cell division and proliferation, immunological activity, vascular proliferation and embryo implantation. Interestingly an over-representation of processes involving vesicles and exosomes was also found. These terms match with previously described processes known to occur at the time of implantation. Cellular matrix remodeling and an increase in vascular proliferation permeability and angiogenesis at the implantation site are one of the earliest prerequisites for embryo implantation (Zhang et al., *Mol Reprod Dev* 2013; 80:8-21). Also intense communication through cell signaling between the embryo and the endometrial cells has been described as part of the embryo-endometrial crosstalk essential for adequate embryonic implantation involving, in some cases, extracellular vesicles/exosomes (Ng et al., *PLoS One* 2013; 8:58502). Also, immune responses have been proven to play important roles in early pregnancy (Altmae et al., 2010; and Haller-Kikkatalo et al., *Semin Reprod Med* 2014; 32: 376-384).

PCA analysis, a dimension-reduction tool that can be used to reduce a large set of variables to a small set that still contains most of the information in the large set, revealed that a subset of 40 of the 85 genes differentially expressed genes, called endometrial receptivity panel A genes could accurately differentiate between LH+2 and LH+7. These genes, listed in FIG. 3A, allow 100% correct classification of endometrial samples from donors into these two status groups. This panel of genes is also able to assess the receptivity status of samples from infertile patients obtained at the secretory phase, classifying samples into: "receptive', this means the WHO matches the day on which the biopsy was taken; "pre-receptive", meaning that the endometrium has not reached its WOI yet or "post-receptive", i.e., this endometrium has already passed its WOI.

Focusing on the technical aspects of the development, high-throughput RT-qPCR was chosen for the analysis of such a panel of endometrial biopsies. RT-qPCR is the most robust and reliable technique currently available for gene expression analysis. Alternative methodologies output such as microarray results and RNA-seq expression data need to be validated using RT-qPCR methods (Mortazavi et al., *Nat Methods* 2008; 5:621-628; and Costa et al., *Transl lung cancer Res* 2013; 2:87-91).

The implementation of endometrial receptivity tests such as the one developed in the present study into the clinical practice routine may help guide embryo transfers to be performed in the best endometrial moment, guaranteeing embryo-endometrial synchrony and thus, allowing for the achievement of better ART results. Couples with repeated implantation failure, previously failed IVF cycles and also couples with recurrent miscarriage would benefit from the detailed analysis of endometrial receptivity and embryo-endometrial synchronization. This study is a new step in the field of personalized medicine in human reproduction in the management of the endometrium in preparation for embryo transfer, with the final goal of achieving better ART results increasing embryo implantation rate and the likelihood of successful pregnancies.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of predicting endometrial receptivity status for embryonic implantation in a human subject, the method comprising:
   (a) providing a first biological sample obtained from a human subject at a first time point within a menstrual cycle;
   (b) determining a gene expression profile of a panel of genes in the first biological sample,
   wherein the panel of genes consists of: Annexin A4 (ANXA4), Cation channel sperm auxiliary subunit beta (CATSPERB), Prostaglandin F receptor (PTGFR), Prostaglandin-endoperoxide synthase 1 (prostaglandin G/H synthase and cyclooxygenase) (PTGS1), Interleukin-8 (IL8), Secretoglobin, family 2A, member 2 (SCGB2A2), Angiopoietin-like 1 (ANGPTL1), Hypoxanthine phosphoribosyltransferase 1 (HPRT1), Matrix metallopeptidase 10 (MMP10), Progesterone Receptor (PGR), Integrin alpha 8 (ITGA8), Interferon gamma (IFNG), Prokineticin-1 (PROK1), Forkhead box protein O1 (FOXO1), C-X-C motif chemokine ligand 1 (CXCL1), Stanniocalcin-1 (STC1), Matrix Metallopeptidase 9 (MMP9), Mucin 1 (MUC1), Ribosomal protein L13a (RPL13A), Calcitonin-related polypeptide alpha (CALCA), Integrin subunit alpha-9 (ITGA9), Rac GTPase-activating protein 1 (RACGAP1), Glutathione peroxidase 3 (GPX3), Protein phosphatase 2, regulatory subunit B, gamma (PPP2R2C), Arginase 2 (ARG2), Secretoglobin, family 3A, member 1 (SCGB3A1), Aldehyde dehydrogenase family 1 member A3 (ALDH1A3), Apolipoprotein D (APOD), C2 calcium-dependent domain-containing protein 4B (C2CD4B), Trefoil factor 3 (TFF3), Aquaporin-3 (AQP3), Gap junction protein, alpha 4 (GJA4), Rho GDP-dissociation inhibitor alpha (ARHGDIA), Selectin L (SELL), Apolipoprotein L, 2 (APOL2), Metallothionein-1H (MT1H), Metallothionein-1X (MT1X), Metallothionein-1L (MT1L), Monoamine oxidase AA (MAOA) and Metallothionein-1F (MT1F) using reverse transcription polymerase chain reaction analysis; and
   (c) comparing the determined gene expression profile in step (b) with a gene expression profile of the same panel of genes listed in step (b) of a receptive endometrial receptivity reference group, a non-receptive endometrial receptivity reference group, a pre-receptive endometrial receptivity reference group, and a post-receptive endometrial receptivity reference group;
   (d) identifying the human subject as having:
      (i) a receptive endometrial status, wherein the determined gene expression profile corresponds to a gene expression profile of the panel of genes of a receptive endometrial receptivity reference group,
      (ii) a non-receptive endometrial status, wherein the determined gene expression profile corresponds to a gene expression profile of the panel of genes of a non-receptive endometrial receptivity reference group,
      (iii) a pre-receptive endometrial status, wherein the determined gene expression profile corresponds to a gene expression profile of the panel of genes of a pre-receptive endometrial receptivity reference group, or
      (iv) a post-receptive endometrial status, wherein the determined gene expression profile corresponds to a gene expression profile of the panel of genes of a post-receptive endometrial receptivity reference group; and
   (e) transferring a pre-implantation embryo into the human subject identified as having a receptive endometrial status.

2. The method of claim 1, wherein the first biological sample is an endometrial biopsy obtained from a uterine fundus.

3. The method of claim 1, wherein the human subject has undergone assisted reproductive treatment, and the first time point is seven days after a luteinizing hormone surge.

4. The method of claim 3, wherein the human subject has undergone hormone replacement therapy cycles, and the first time point is five days after progesterone impregnation.

5. The method of claim 1, wherein the human subject has undergone assisted reproductive treatment, and the first time point is seven days after administration of human chorionic gonadotropin (hCG).

6. The method of claim 1, further comprising after identifying the human subject as having a non-receptive endometrial status, a pre-receptive endometrial status, or a post-receptive endometrial status, (f) obtaining a second biological sample from the human subject at a second time point and repeating steps (b), (c), and (d) on the second biological sample.

7. The method of claim 6, further comprising after identifying the human subject has having a receptive endometrial status, (g) transferring a pre-implantation embryo into the identified human subject.

8. The method of claim 6, wherein the second biological sample is an endometrial biopsy obtained from a uterine fundus.

9. The method of claim 6, wherein the subject is identified as having a post-receptive endometrial status, and the second biological sample is obtained in another menstrual cycle one or two days earlier in the another menstrual cycle as compared to when the first biological sample was taken in the previous menstrual cycle.

10. The method of claim 6, wherein the subject is identified as having a pre-receptive endometrial status, and the second biological sample is obtained in another menstrual cycle one or two days later in the another menstrual cycle as compared to when the first biological sample was taken in the previous menstrual cycle.

11. The method of claim 6, wherein the subject is identified as having a non-receptive endometrial status, further comprising instructing a healthcare professional to select a treatment plan for the identified subject.

12. The method of claim 6, wherein the subject is identified as having a non-receptive endometrial status, further comprising selecting a treatment plan for the identified subject.

13. The method of claim 12, wherein the treatment plan comprises a hormone replacement therapy cycle.

14. The method of claim 1, wherein the subject has a history of miscarriages or stillbirths, and/or a history of fertility issues.

15. The method of claim 1, wherein the subject has had one or more cycles of in vitro fertilization (IVF).

16. The method of claim 1, wherein the subject has previously not had IVF.

17. The method of claim 1, wherein the determining step occurs on a chip, an array, a multi-well plate, or a tube.

18. The method of claim 1, wherein the determining step of each gene within the panel of genes is performed in a reaction volume of 0.005 µL to 100 µL.

19. The method of claim 1, wherein the determining step of each gene within the panel of genes is performed in a reaction volume of 0.005 µL to 50 µL.

20. The method of claim 1, wherein the determining step is performed using a computer-assisted algorithm.

21. The method of claim 1, wherein the comparing step is performed using a classification model, wherein the classification model is principal component analysis and/or discriminant functional analysis.

22. The method of claim 1, further comprising modifying the subject's clinical record to identify the subject as having a receptive endometrial status, as having a non-receptive endometrial status, as having a pre-receptive endometrial status, or as having a post-receptive endometrial status.

23. The method of claim 22, wherein the clinical record is stored in a computer readable medium.

* * * * *